(12) United States Patent
Peterson

(10) Patent No.: US 6,641,562 B1
(45) Date of Patent: Nov. 4, 2003

(54) APPARATUS AND METHOD OF INTRAVENOUS FLUID INFUSION

(75) Inventor: Dean McCormack Peterson, Escondido, CA (US)

(73) Assignee: HPS Medical, Inc., Edina, MN (US)

( * ) Notice: Subject to any disclaimer, the term of this patent is extended or adjusted under 35 U.S.C. 154(b) by 0 days.

(21) Appl. No.: 09/567,966

(22) Filed: May 10, 2000

(51) Int. Cl.$^7$ ............................................. A61M 37/00
(52) U.S. Cl. ........................ 604/141; 604/65; 604/132; 604/133; 604/246
(58) Field of Search ...................... 604/65–67, 131–133, 604/140, 141, 150, 151, 153, 246, 408–409

(56) References Cited

U.S. PATENT DOCUMENTS

| | | | |
|---|---|---|---|
| 4,187,847 A | 2/1980 | Loeser | 128/214 |
| 4,230,244 A | 10/1980 | Zissimopoulos | 222/450 |
| 4,335,835 A | 6/1982 | Beigler et al. | 222/95 |
| 4,361,147 A * | 11/1982 | Aslanian et al. | 604/249 |
| 4,641,522 A | 2/1987 | Lopresti | 73/261 |
| 4,714,462 A | 12/1987 | DiDomenico | 604/67 |
| 4,735,613 A * | 4/1988 | Bellin et al. | 604/141 |
| 4,825,707 A | 5/1989 | Rosaen | 73/861.77 |
| 4,900,305 A | 2/1990 | Smith et al. | 604/65 |
| 5,032,117 A * | 7/1991 | Motta | 604/246 |
| 5,049,141 A | 9/1991 | Olive | 604/891.1 |
| 5,184,519 A | 2/1993 | Ciarelli et al. | 73/861.77 |
| 5,207,666 A | 5/1993 | Idriss et al. | 604/891.1 |
| 5,211,626 A | 5/1993 | Frank et al. | 604/65 |
| 5,308,335 A * | 5/1994 | Ross et al. | 604/67 |
| 5,348,539 A * | 9/1994 | Herskowitz | 604/141 |
| 5,399,166 A | 3/1995 | Laing | 604/146 |
| 5,938,636 A | 8/1999 | Kramer et al. | 604/66 |
| 5,980,501 A | 11/1999 | Gray | 604/408 |
| 6,290,681 B1 * | 9/2001 | Brown | 604/65 |

* cited by examiner

Primary Examiner—Gregory L. Huson
Assistant Examiner—Tuan Nguyen
(74) Attorney, Agent, or Firm—Mark A. Litman & Assoc. P.A.

(57) ABSTRACT

An infusion system packaged in a light weight nylon portable mesh container, which is also the pump of the system, includes a removable therapy bag holding the Rx to be infused into the patient. A bladder within the pump is inflatable to provide pressure onto the therapy bag to aid in the discharge of the Rx. When filling the therapy bag, the pharmacist, using his computer to comply with standards, simultaneously programs an EPROM with data specifying the Rx as well as instructions for dispensing the Rx. In one embodiment of the invention, the EPROM fits into a docking receptacle in the pump, while in a second embodiment the EPROM is integral with the therapy bag. A microcomputer mounted in the pump is programmed to control the flow of the Rx to the patient, reading the data from the EPROM in generating the control signals. The microcomputer cyclically drives a fluid control module which outputs a fixed amount of Rx for each cycle of operation. Three fluid control modules are disclosed; a cavity which deliver a bolus of Rx for each rotor rotation, or a shuttling longitudinally displaceable "cork" positioned in the output connector of the therapy bag, or a squeezed tube. Flow is monitored, and alarm interrupts to the microcomputer are provided for flow failure generating appropriate alarms. An alarm shuts down system operation and alerts the patient by means of visual messages on the microcomputer display and by an audible alarm. A buffer memory in the pump stores data relevant to such a mishap for later examination to determine responsibility and cause. Data is tied to a real-time clock (date and time).

8 Claims, 13 Drawing Sheets

APPARATUS AND METHOD OF INTRAVENOUS FLUID INFUSION

BACKGROUND OF THE INVENTION

1. Field of the Invention

This invention relates to administration of a medicinal fluid to a patient and, in particular, to low-cost, easy-to-use infusion systems for the intravenous dispensing of a fluid prescription.

2. Description Relative to the Prior Art

A wide variety of infusion systems are presently known in the medical art, particularly within the field of technology directed towards therapies requiring the use of intravenous medication. The administration of medication by intravenous delivery as prescribed by a medical doctor may be dispensed to the patient by an infusion system for certain therapies. The prescribed therapeutic liquid is referred to as the prescription or "Rx", and is usually supplied by a pharmacist in a container such as a disposable plastic bag for use with an infusion system. The plastic bags usually have attached to them various components or elements which are useful in the infusion process such as various tubes and elements to secure the bag in place, to transport liquids (e.g., prescriptions, water, nutritional supplements, analyze solutions, etc.) with respect to the patient, to support the elements of the container, etc. This composite arrangement is usually referred to in the medical art as a "set". The set is then loaded into a fluid delivery device called the "pump" either by a nurse or by the patient himself. Once the pump is connected to the patient, the device pumps the Rx through the conveying tubes of the set to infuse the patient.

The assembly of an infusion system, as presently known in the art, requires a certain degree of skill and manual dexterity. In some conventional infusion systems, the tubing of the set must be loaded into the pump, the set cleared, the set tubing meshed between rollers, and the roller gate closed. In a hospital setting, a nurse or medical technician is generally available to perform these dexterous steps and to instruct and/or supervise the patient in the loading and operation of the pump. It is also necessary for the physician, nurse or patient to program the rate of pump operation to control the fluid flow rate of the medication to the patient. Written records of the infusion system parameters must be generated and maintained for various medical reporting reasons. In the present day medical setting, many ill people are out-patients who must set up and operate their infusion system at home without the services of a knowledgeable practitioner to oversee proper assembly and performance of the system. Some patients may have debilitating illnesses or impacted conditions of memory dysfunction which leave them too weak or too forgetful to carry through complex assembly and programming procedures. With a rapidly growing aging population, many out-patient seniors may not have either the manual dexterity, physical strength, or mental acuity needed to cope with the demands of setting up and using current infusion systems. Additionally, with the downward economic pressures on all medical costs, and especially those of Medicare and Medicaid, a need exists for reducing the costs of these therapeutically essential infusion systems and minimizing the cost of technical assistance personnel.

U.S. Pat. No. 5,935,099 describes a menu driven reprogrammable drug pump is provided with a memory, such as flash memory, a display, a keyboard, and a communications port to allow a generic pump to be programmed with a desired pump application (therapy) program and patient specific settings. Programming and data transfer with another pump or a computer to and from the patient pump is by the communications port that allows local and/or remote communications with the pump. Flash memory stores the pump application program during use. Patient safety is provided by a cassette identification system, an occlusion detection system, and a latch/lock detection system. Automated testing of the pump is by a closed loop testing system. This system does not provide for unique pump identification, in combination with unique patient and therapy information. A limited range of pumping systems is also disclosed.

The present invention alleviates problems present in the prior art by providing a simplified, low-cost infusion system adapted for use both by in-patients in hospitals and by out-patients at home.

SUMMARY OF THE INVENTION

A therapy infusion apparatus for delivery of medicinal fluid to a patient may comprise:
 a) a flexible therapy bag,
 b) a movable surface which can apply force to an outside surface of the therapy bag to increase fluid pressure within said therapy bag,
 c) an exit port in the therapy bag which will allow fluid to exit in a delivery direction from the flexible therapy bag under fluid pressure,
 d) an adjustable, fluid control element located along the delivery direction, after the exit port.

The therapy infusion apparatus may be constructed with the therapy bag having at least one major face which comprises at least 25% of the total surface area of the therapy bag, and the movable surface can be moved into contact with the at least one major surface so that contact between the at least one major surface and the movable surface covers at least 50% of the surface area of the at least one major surface by the time that the movable surface is fully extended. The therapy bag may comprise at least two fluid flow ports within a fluid control element, one of the ports comprising the exit port, and adjacent to at least one of the ports is an element which has a storage area for a memory unit and access ports to the memory unit. The memory unit may comprise, for example, a chip (e.g., intelligence chip), and the access ports enable electronic connection from an outside memory reading or memory writing apparatus to the chip. The chip may be present within the storage area, and the chip preferably contains electronically readable information relating to at least two different topics selected from the group consisting of the prescription; the name of an active ingredient in the prescription; the chemical name of a prescription carrier; additives in the prescription; volume of the prescription; expiration date; name of a prescribing doctor; name of a private loader; name of a local supplier/manufacturer of ingredients of the prescription; source of at least some materials in the prescription; a name of a therapy bag manufacturer; a name of a pharmacist; a patient name; patient information relating to at least one of age, allergies, address, frequency of prescription refill, weight, chemical intolerances, instructions for a flow control module with respect to desired flow rates; intervals for delivery; rate and volume of delivery; and drip rate.

The therapy infusion apparatus preferably provides the movable surface as an extendable bladder which is expandable or inflatable by a fluid (e.g., liquid or gas) to move a surface of the bladder against a surface of the therapy bag.

A therapy bag for use in the infusion of liquids to a patient is described comprising a flexible bag having a storage area and a delivery end, the delivery end comprising at least two fluid ports, at least one port capable of allowing fluid from within said storage area when pressure is applied to liquid within the storage area, and the delivery end also having a storage area for storage of a memory element, the storage area having access ports for electronically accessing the memory element. The storage area preferably contains a memory storing element such as a chip and there are electronic access ports oriented in the storage area to allow external electronic access to the chip so that information on the chip may be accessed. The storage area may be asymmetrically located along the delivery end. At least two liquid flow ports may be located to one side of the asymmetrically located storage area. A battery may be located on the same side or the other side of the ports as the storage area for the memory unit. The battery may provide power to any electrical or electronic element on the pump or apparatus, such as at least one electrically powered element on the therapy bag selected from the group consisting of a display panel on the pump, a chip, a fluid rate control element, and an alarm (e.g., sound display, light display, vibration display, Radio Frequency signal, electronic signal with a connection to computer or communication system).

The infusion system of the invention is packaged in a structured support system, such metallic, polymeric, or other structural housing such as a light-weight nylon mesh container which houses basic components of the infusion device. The container, which is the system pump, may be provided with elements to secure the container to a patient. These patient attachment elements include belts, straps, harnesses, hooks, and associated apparel (e.g., a shirt, jacket, girdle, side-pack, back pack or the like having the container secured to a portion thereof or in a pocket). A preferred support element comprises a loosely overlying garment such as a harness, shoulder belt, waist belt, side-pack or backpack, such as one constructed of fabric, such as nylon straps, so the apparatus may be worn by an ambulatory patient. The container alternatively may be suspended from a fixed support for the patient immobilized in bed, in a chair or a vehicle.

A filled therapy bag containing the Rx to be infused into the patient is associated with the pump, causing a fluid connection element between the Rx and the pump as by insertion into the pump by the medical practitioner, such as by a physician, attendant, nurse or by the patient. With the therapy bag positioned in the pump, a movable (force-providing) surface (such as an inflatable bladder or moving wall element or moving plate located within the walls of the container, as for example with the therapy bag placed against an element) moves within the container walls to increase pressure to the Rx within the therapy bag. The pressure against the therapy bag may be provided by any element, especially any non-puncturing element adjacent to or comprising an interior wall of the pump which is in face-to-face (major surface or side-to-side) contact with the Rx filled plastic therapy bag. Force provided by against the inflated bladder provides the pressure within or on the prescription bag which enables the flow of the medication through the set.

An Electronic Control Unit (ECU), in the form of a semiconductor microcomputer, and its battery power supply are located within the structural housing, preferably within the pump's assembly, as in a pocket, sleeve, housing, frame, pouch, lining or container of the pump. The ECU plugs into an element which connects memory or circuitry to the infusion system or within the set as with electrical wires, cables, plugs, connectors or printed circuit cable which electrically interconnects the various components of the system. The ECU has the potential to perform the functions of controlling the sequences of operation of the system and components, monitoring the performance of the system and individual components, and alerting the patient or a health supervisor of any noteworthy condition or malfunction of the infusion system or any part thereof. The ECU may include a ROM containing the microcomputer's operating system, as well as operational programmed routines which include displaying data relating to the system status by means of visual display unit, such as an LED, LCD or other visual display which may be mounted on the pump, visible to the patient. The status data being stored in the ECU memory is also available for visual display on a monitor (CRT, LED, LCD, etc.) or later printout, even by means of a modem so that the information may be transmitted to a medical control station distant form the patient.

A fluid control module (FCM) may also be part of the set. The FCM comprises an inlet port, an outlet port and a frame. Its inlet port is to be connected to the therapy bag and its outlet port supplying medication to the patient is connected to intravenous tubing segment of the set by means of connectors such as male-female connectors, slidable inserts, clamped tubes, or hydraulic push-on connectors. Mounted in the FCM may be an electronically connectable source of information such as a chip, hardware, software source or semiconductor plug-in EPROM having encoded within it information such as information concerning the therapy medication, its dosage, rate of delivery, schedule of delivery, and other information which may relate to the patient and treatment. The software would be specifically designed for this operation, allowing ready access to insertion of therapy specific, patient specific, and pump specific information. Additional specific information may be accessed such as required storage conditions, actual storage conditions (e.g., a thermocouple could be read to show conditions during transit), and the like may also be addressed by the software. At the time of filling the prescription, the pharmacist enters the information into the source of information such as the EPROM chip by whatever information insertion means are available, such as by replacing a chip, loading a chip from or with his computer. The address bus of the ECU may be interconnected with an EPROM via an electrical printed circuit cable so that the ECU has access to the data and instructions stored in the EPROM relating to the specific bag therapy. A data storage element may be provided with a General Purpose Interface Buss (GPIB) for receiving and selection of appropriate data from the pharmacists required input. This information will be loaded onto the chip resident in the fluid control module. The information will usually be loaded at the tome that the therapy bag is being filled.

With the therapy bag and attached FCM loaded into the pump system, operation commences in one or two different manners. In one format, operation may start only after a security routine within the system (either hardware or software) checks to assure that a therapy code on the therapy bag and/or FCM matches a code in the pump. This assures that the therapy bag being loaded or inserted in or onto the pump is the proper therapy. After clearance by the security check, the operation may begin. An alarm or indicator may be provided to indicate an improper connection or record of misconduct in the use of the wrong therapy in the bag. These events may also be recorded in the pump buffer. Another format would begin operation when the "start" button is depressed or a timed signal initiates the operation (e.g., from data in the EPROM). The coding in the EPROM is read by the ECU and a signal is sent to the FCM locking it up so that fluid cannot flow until such direction is given or allowed. Elements are provided to expand the bladder to a pressure level prescribed by pump logic so that contained liquid may be put under pressure. The pressing of the bladder may be by a plate or surface coming into contact with the exterior of the bladder, a collar moving along a surface of the bladder or any element which attempts to compact the space within the bladder. For example, a small air compressor under control of the ECU supplies air to the bladder whose pressure is monitored by a pressure transducer. The air compressor is cycled on and off by the microcomputer to maintain bladder pressure in accordance with the pressure value required by the Rx and encoded in the EPROM. A start-up program enables the user to bleed air out of the system when desired (even before fluid is actually pumped), and a message may be provided on the display of the ECU would then advise the user that the batteries are OK, and that the system may be connected to the patient's body. With the intravenous connection made, the patient may then push the start button, and the programmed delivery is begun. Under control of the ECU, the FCM meters the flow of the medication by cyclically dispensing precise volumes of fluid through its outlet port. Each cycle of the FCM generates a signal pulse which is detected (e.g., simply by a counter, flow-meter, pulse meter, or other sensor meter) or by a detector such as a Hall-effect sensor, a photodiode or the like and the sequence of events or pulses is monitored by the ECU. Any failure in flow would cause an interruption of the stream of pulses from the Hall-effect sensor (or other sensor), and result in a shutdown of the system (the interruptions were designated as sufficiently extreme) and initiation of an alarm sequence by the ECU as will be explained below. Also, when a system shutdown occurs, a check valve in the set line to the patient's body may actuate to preclude any back leakage from the patient's circulatory system into the infusion system.

In the case of infusion of analgesics, a patient controlled analgesic (PCA) button on the ECU cooperates with the logic control loop to a) check with a buffer to see if patient controlled administration of the analgesic is permitted; b) if PCA is permitted, at what delivery rate or amount, the number of PCA's, etc.; c) permit the patient to enhance or beef-up the paint control or the rate of administration in accordance with the steps outlined above, and provide a confirming signal (e.g., a sound signal); and d) in some cases, no Rx may be delivered, but the sound signal can be given as a placebo.

The elements of the infusion system may be assembled and programmed to operate either open loop or closed loop.

BRIEF DESCRIPTION OF THE DRAWINGS

FIGS. 11–14c are drawings of alternative embodiments of a fluid control module in accordance with the invention.

DETAILED DESCRIPTION OF THE INVENTION

Figure 1:
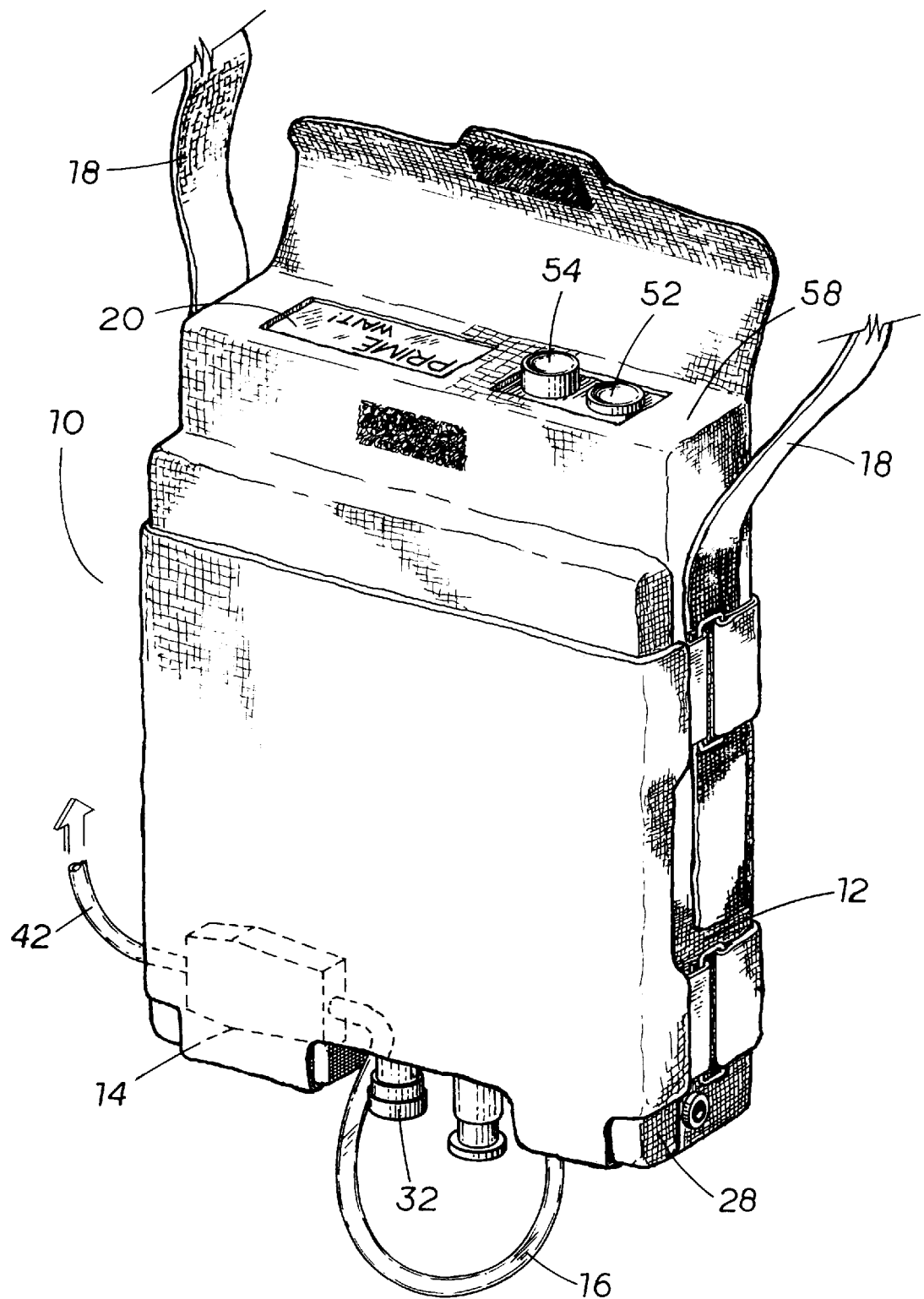
FIG. 1 is a drawing of a packaged infusion system within the scope of the invention.

The use of prescription delivery bags or pouches for the dispensing of fluid prescriptions or supplements should entail a number of properties to be acceptable to the medical profession and to the user. The delivery system must provide dependable delivery of prescribed materials, the system should be capable of use with minimal potential for error, the system should enable patients rather than highly skilled medical personnel to connect and operate the system, the system itself should operate to minimize errors in the delivery of the correct prescription, and patients desire to have delivery systems which are less conspicuous. The present invention is able to address some of these concerns and provide a dependable, easy to operate, inconspicuous prescription bag delivery system.

There are four distinct areas of technology or components in the practice of the present invention which operate together to form the delivery system of the present invention. Each of these components comprise inventions capable of independent as well as system invention according to the present invention. Those areas include 1) the pouch containing the liquid material to be delivered by infusion (e.g., intravenously) to a patient, 2) a fluid control mechanism (FCM) (which may be incorporated into or onto the pouch containing the liquid to be delivered, 3) an electronic control module (ECM), and 4) a housing for the pouch, FCM and ECM.

The invention includes a therapy infusion apparatus for delivery of therapeutic fluid to a patient, the apparatus comprising:

a) a flexible therapy bag, b) a movable surface which can apply force to an outside surface of the therapy bag to increase fluid pressure within the therapy bag, c) an exit port in the therapy bag which will allow fluid to exit in a delivery direction from the flexible therapy bag under pressure, d) an adjustable, fluid control element located along the deliver direction, after the exit port.

The therapy bag of the infusion apparatus may have at least one major face with a movable surface which movable surface comprises at least 25% of the total surface area of the therapy bag, and the movable surface can be moved into contact with the at least one major surface so that contact between the at least one major surface and the movable surface covers at least 50% of the surface area of the at least one major surface by the time that the movable surface is fully extended. The movable surface preferably comprises an extendable bladder. The bladder may be expandable or inflatable by a fluid (preferably a liquid) to move a surface of the bladder against a surface of the therapy bag. The therapy bag may, for example, comprise at least two fluid flow ports within a fluid control element, one of the ports comprising the exit port, and adjacent to at least one of the ports is an element which has a storage area for a memory unit and access ports for accessing information from a memory unit within the storage area. The memory unit preferably comprises a chip, and the access ports enable electronic connection from an outside memory reading or memory writing apparatus to the chip. The therapy infusion apparatus may have a chip present within the storage area, and the chip would contain electronically readable information relating to at least two different topics of information selected from the group consisting of a prescription for the therapeutic material; the name of an active ingredient in the prescription; the chemical name of a prescription carrier; additives in the prescription; volume of the prescription; expiration date; name of a prescribing doctor; name of a private loader; name of a local supplier/manufacturer of ingredients of the prescription; source of at least some materials in the prescription; a name of a therapy bag manufacturer; a name of a pharmacist; a patient name; patient information relating to at least one of age, allergies, address, frequency of prescription refill, weight, chemical intolerances, instructions for a flow control module with respect to desired flow rates; intervals for delivery; rate and volume of delivery; and flow rate as a function of time (the prescription program). The system of the invention may have various elements, subelements, components and subcomponents that are disposable after a single use or a few uses. The relative low cost of the elements enables this disposability, just as the need to avoid cross-contamination between patients and the need to prevent storage contamination of components makes replacement desirable.

The therapy bag for use in the infusion of liquids to a patient may comprise a flexible bag having a storage area and a delivery end, the delivery end comprising at least two fluid ports, at least one port capable of allowing fluid from within the storage area when pressure is applied to liquid within the storage area, and the delivery end also having a storage area for storage of a memory element, the storage area having access ports for electronically accessing the memory element. The storage area may be asymmetrically located along the delivery end. There may be at least two liquid flow ports are located to one side of the asymmetrically located storage area. The pump may have a battery (preferably a replaceable battery) as an element therein. The battery is used at least to provide power at least to the chip (and any servomechanical or electromechanical or electrical elements within the system). The battery may also provide power to at least one electrically powered element on the pump or therapy bag selected from the group consisting of a display panel, a chip, a fluid rate control element, and sound alarms.

The therapy infusion apparatus may further comprise
  e) a fluid flow detector that determines at least whether therapeutic fluid is flowing through, towards or past the exit port;
  f) a meter measuring flow rates of the therapeutic liquid within or out of the therapy infusion apparatus; and/or
  g) an alarm that activates upon malfunctioning or interruption of any defined function of the therapy infusion apparatus during loading of a therapy bag or delivery of therapeutic liquid to a patient or movement of therapeutic liquid within the therapy infusion apparatus.

The therapy infusion apparatus may further comprise a microcomputer for controlling at least one operating function of the infusion apparatus.

The memory chip in the infusion therapy apparatus is programmable by an auxiliary computer external to the infusion apparatus, whereby information may be entered for storage in the chip relating to the therapeutic fluid.

The therapy infusion apparatus may also have a pump present within the apparatus which pump comprises:
  a) flexible enclosure member wherein the elements comprising the infusion apparatus are mounted,
  b) a bladder located in the pump, wherein when the therapy bag is positioned in the pump the surfaces of the therapy bag are substantially in contact with the bladder,
  c) air compressor for inflating the bladder,
  d) pressure transducer for measuring the air pressure in the bladder, and
  e) a vent for controllably venting the bladder.

The apparatus may further comprise a meter measuring quantities of therapeutic fluid and the meter comprises:
  a) a shell having an interior cavity, the cavity having an input port for accepting the medicinal fluid from the therapy bag and an output port for transferring the medicinal fluid out to the patient,
  b) first and second axles parallelly mounted in the cavity,
  c) first and second longitudinally extending rotors,
  d) first and second fixed bar magnets mounted with the axes of the magnets directed along the longitudinal axis of the first rotor, the first rotor having a first cycloidal contour,
  e) third and fourth fixed bar magnets mounted with the axis of the magnets directed along the longitudinal axis of the second rotor, the second rotor having a second cycloidal contour, the first and the second rotors rotatably mounted on the first and the second axles, wherein the longitudinal axis of the first rotor is perpendicular to the longitudinal axis of the second rotor, and a portion of the first cycloidal contour is substantially in contact with a portion of the second cycloidal contour,
  g) the shell having an interior wall in the shape of a continuous closed curved surface,
  h) the first rotor having a portion of its contour in contact with the wall, the second rotor having a portion of its contour in contact with the wall, wherein a first chamber is formed bounded by the first rotor the second rotor and the wall, and a second chamber is formed bounded by the first rotor the second rotor and the wall, the first chamber containing the inlet port and the second chamber containing the outlet port,
  i) a reciprocating shuttle proximate the shell, the shuttle comprising movable fifth and sixth magnets, the fifth magnet for interaction with the first and second magnets when the shuttle is actuated to position the fifth magnet to attract the first or the second magnet allowing rotation of the first and the second rotors, and the sixth magnet for interaction with the third and the fourth magnets when the shuttle is actuated to position the sixth magnet to attract the third or the fourth magnet allowing rotation of the first and the second rotors, whereby for each quarter rotation of the first and the second rotors a fixed quantity of medicinal fluid is forced from the second chamber through the outlet port, and j) electromagnetic actuating means for alternately driving the shuttle back and forth, the electromagnetic actuating means under control of the microcomputer.

The outlet port may include a check valve opposing fluid flow back into the cavity, and the meter may comprise a rate of magnetic field change electrical transducer. The alarm system may be activated by a microcomputer responsive to a fluid flowing through the meter. The infusion apparatus may also comprise either h) a display driven by the microcomputer, the display visually indicating any defined apparatus malfunction, or b) an audio system driven by the microcomputer aurally indicating any defined apparatus malfunction.

The therapy infusion apparatus may further comprise:

d) alarm information available from the microcomputer as input to a modem for transmission over an external communication line.

A method of infusing a medicinal fluid to a patient may comprise the steps of:

a) filling a therapy bag with the medicinal fluid, b) recording on a semiconductor EPROM the characteristics of the fluid and the necessary information related to infusing a patient with the fluid, c) reading the information from the EPROM by a microcomputer, d) generating control signals in accordance with the information by the microcomputer, and e) activating a fluid dispensing unit in response to the control signals, whereby the fluid dispensing unit infuses the patient with the medicinal fluid through set tubing in accordance with the recorded information.

Figure 3B:
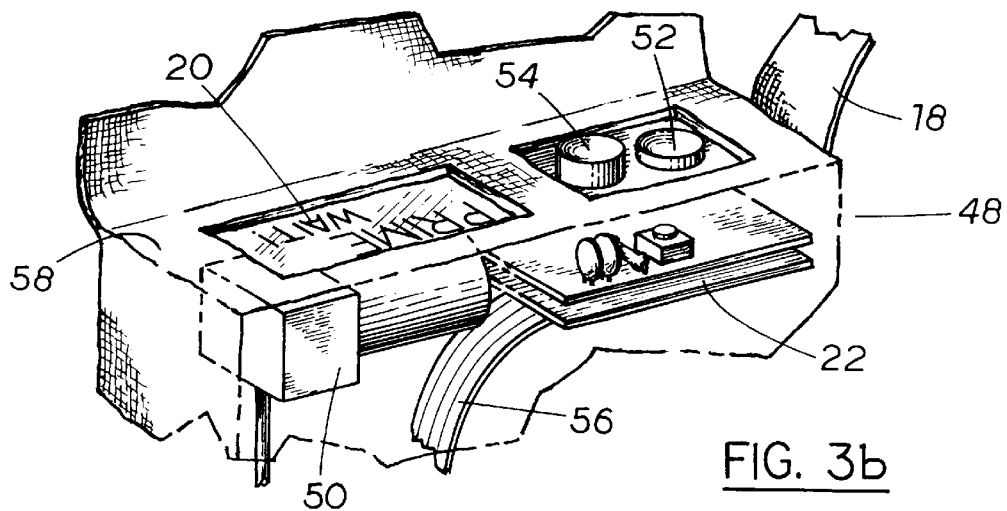
FIG. 3b is a drawing showing the location of electronic components of the invention.
Figure 3A:
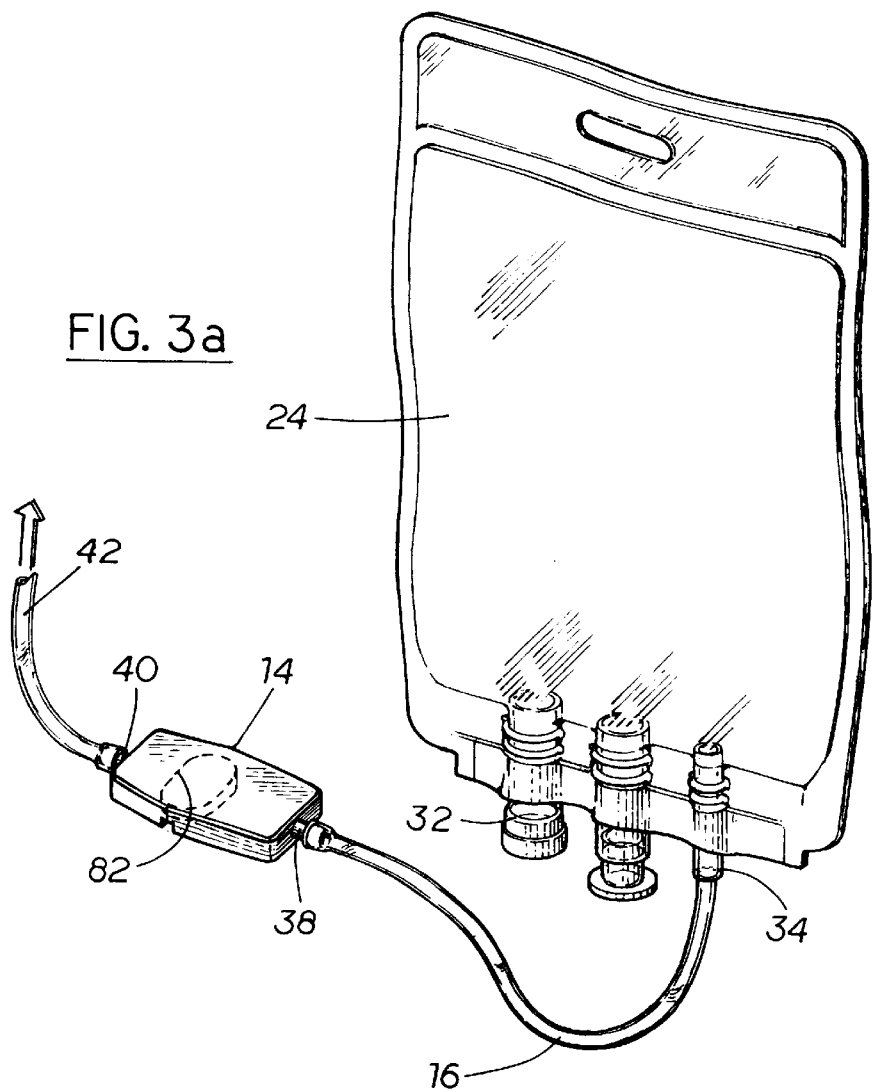
FIG. 3a is a drawing of the therapy bag of the invention and associated interconnecting units.
Figure 9:
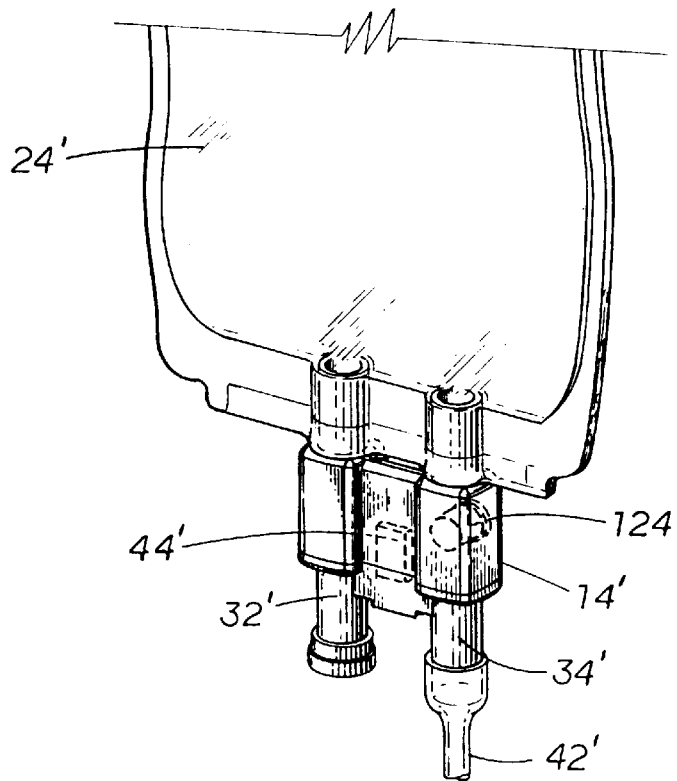
FIG. 9 is a drawing of a second embodiment of the therapy bag of the invention.

A relatively standard therapy bag or pouch 24 for the transportation of prescribed material to a patient for infusion is shown in FIG. 3*a*. The therapy bag 24 is shown with three ports, a fill port 32 (through which the pharmacist or other medical personnel can fill the therapy bag), an access port 34 (from which a liquid conductive lead or tube lead going to a patient is connected), and an optional testing port 39 from which sample may be drawn for preliminary testing, if desired. On the other hand, FIG. 9 shows a therapy bag more consistent with the practice of the present invention. The therapy bag 24' still has a fill port 32' and an access port 34' leading to and from the storage area 33 of the therapy bag 24', but a fluid control mechanism (FCM) 14' is shown associated with both the fill port 32' and the access port 34'. The FCM 14' contains an accessible source of information such as a chip 44' or microchip or other information storage element within the FCM 14'. This accessible information is accessed by an electrical or electronic connection to a device capable of reading the information (e.g., computer, CPU, circuit board, etc.). A flow control valve 124 or valve port 124 is also shown within the access port 34'. It is to be noted that the center of the space between the two ports 34' and 32' are not symmetrical to the edge 31 of the therapy bag 24' to which they are connected. This is a desirable, but optional, design feature that will be explained later. A tip 42' or connection to tubing is shown on access port 34'. The structural features 27 and 29 are merely convenient representations of one style of housing in the FCM 14'. The relatively square features are matters of choice, not required function, although the rear portions 37' of the flush receiving grooves 35' may be fitted so that these elements nest easily together. A central segment 35' of the FCM 14' houses the accessible source of information, here shown as a chip 44'. Four pin access holes 37 (collectively) are shown on the end 39 of the central portion 35 of the FCM 14'. The pin holes 37 are engaged by pins (not shown) which electronically or electrically connect the chip 44 to a device which can read information from the chip 44'. In the practice of the present invention, 10 a small buffer memory or memory access unit (not shown in this figure) may be in another part of the system electrically connected to the chip 44' during operation of the system. The chip 44' may also be connected to a memory or device capable of reading the information on the chip 44' such as a personal computer or integrated home security system or telephone or cable connection which may access a distant information reading system. For example, a modem may be available on a telephone which can accept wires from the pins 37 and transmit the information read from the chip 44' to a central location, as well as connecting the pins 37 to a more local source within the system or available for access by the system.

Figure 10:
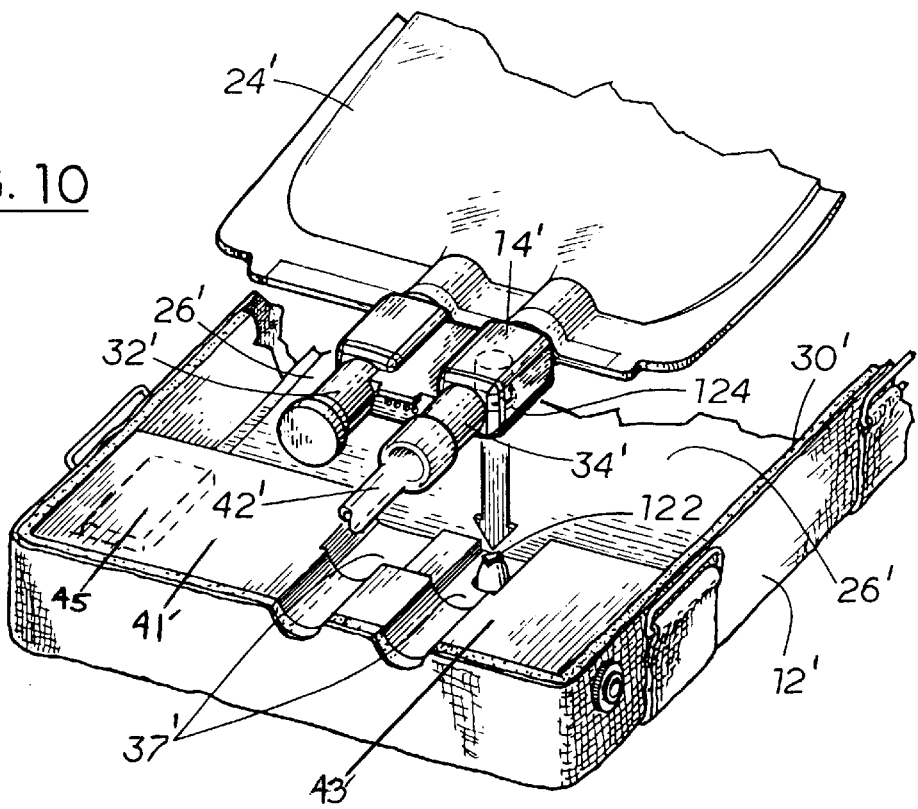
FIG. 10 is a drawing of the therapy bag of FIG. 9 positioned for insertion in the infusion system of the invention.

As noted earlier, the spacing outside of the area covered by the FCM 14' access port 24' and input port 32' may be unequally distributed. As shown in FIG. 10, the areas 41' and 43' adjacent to the flush receiving grooves 35' are not of equal dimensions. Here it is shown (by way of example) that the panel area 41' is bigger than panel area 43'. The purpose for this is to enable the placement of additional components underneath the panels 41' and 43' with fewer restrictions in size. For example, a much larger (and therefore more likely to be a more longer lived) energy source may be placed under panel 41' than if panel 41' were the same size as panel 43'. Similarly, as motors may be small without sacrificing their ability to perform any necessary functions, they may be located under panel 43' while preserving the larger space desirable for the energy source and other elements which may be placed under panel area 41'. As shown in FIG. 10, a valve port 124 is shown receiving a rotatable stopper 122 which can be driven by motor (not shown) under panel area 43' and powered by a battery 45 under panel area 41'. The motor may cause the rotatable stopper 122 to rotate to open or close the flow or passage of liquids within the access port 34'. Upon appropriate signaling, as from the information stored on the chip 44' delivered to the motor.

Figures 14A, 14B, 14C:
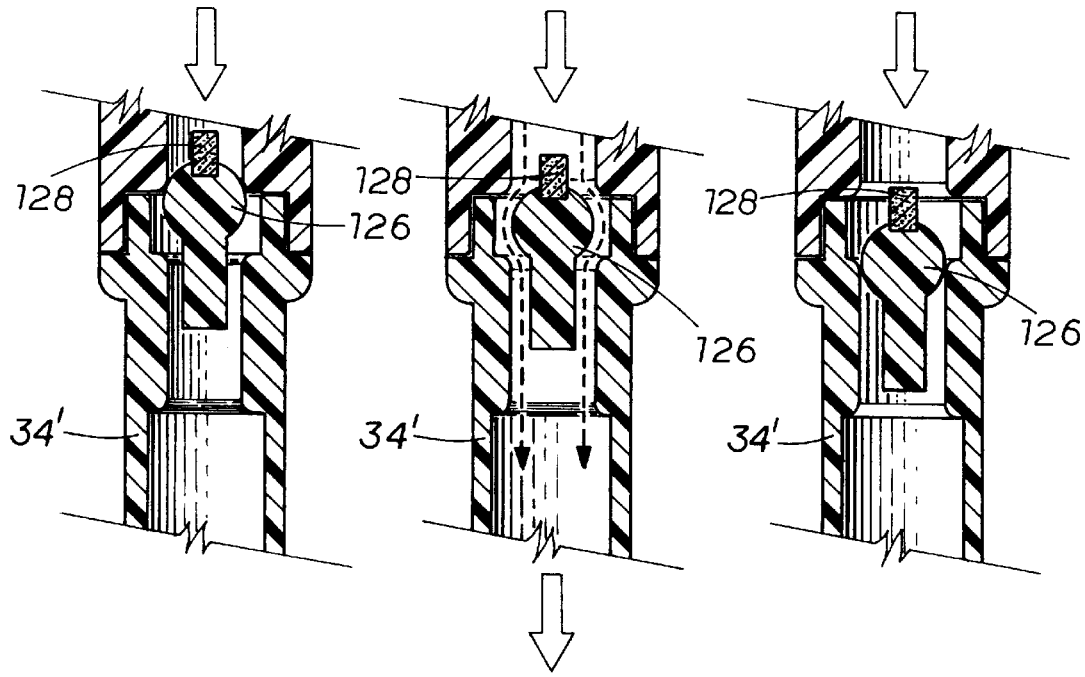

The chip 44' may be inserted into the central area 35 (or an adjacent area with respect to either of the ports 32' and 34') and be secured by natural tension or pressure against the sides of the chip 44'. Any other normal securement means, such as placing grooves on the side(s) of the chip which slide along raised areas or snap into projections, clips, a flange may open to receive the chip and then snap into place to lock in the chip 44', posts which slide through the shell of the central area 35 into holes in the chip, and the like may also be used. It is preferred that upon assembly of the unit and system and placement for use by (e.g., on) a patient, that the pin access holes 37 face in a downward direction (meaning that the access port 34' also faces downwardly. This allows gravity to assist the flow of liquid within the storage area 33 of the therapy bag 24' and to remove any air or other gases which may be present within the storage area 33 from the access port 43'. It is also possible to use the flow of liquid through the valve port 124 to control opening of the valve port in part by gravity although usually a tensive or tension producing element (e.g., spring, magnet, elastic element, etc.) may be used to keep the valve port 124 closed while fluid pressure from a pump (not shown) forces the valve mechanism open. An example of a system with a magnet (to provide attractive force in a desired direction) and cork (to provide buoyancy forces) as such closure mechanisms for valve ports is shown in FIGS. 14*a*, *b* and *c*. As noted, such forces may readily be substituted by springs, electromagnetic forces, electrostatic forces, elastic elements, and the like.

The chip inserted into the FCM may contain whatever information may be important or thought to be important by the pharmacist, doctor and/or patient. The nature and content of the information placed onto the chip is also indicative of aspects of the present invention. For example, before insertion into the FMC (or after insertion, before, during or after loading of the therapy bag), information such as 1) the prescription, including the active ingredient (e.g., drug), carrier, additives, volume, expiration date, doctor, private loader (distal pharmacist), local supplier/manufacturer, laboratory source of materials, therapy bag manufacturer, pharmacist, patient name, patient information (e.g., age, allergies, address, frequency of prescription refill, weight, chemical intolerances, and other information which may even be automatically downloaded from a background source of patient information), instructions for a flow control module (e.g., dependent upon the model and/or manufacturer, and even age of the unit) with respect to desired flow rates, intervals for delivery, rate and volume of delivery, drip rate, and the like.

FIG. 10 also shows features of particular embodiments of an FCM which may be used in the practice of the present invention. For example, the FCM 14' is shown already inserted into the therapy bag 24' at the time that the therapy bag 24' and the FCM 14' are placed into the housing 12' and nestled within the flush receiving grooves 35'. In this way, the therapy bag 24' has been provided with the information in the chip 44' from the point of delivery of the therapy bag 24' as opposed to attempting to separately supply the chips. The FCM and the bag from different sources. It is possible that the chip, FCM and bag may be shipped together and connected at the point of use (at home, office, hospice, residence of care, or hospital), but this merely adds to the complexity of use, rather than reducing that complexity.

It is well known within the medical and pharmaceutical industry that mislabeling, misadministration, misdosage, and/or misuse of pharmaceuticals, including those delivered in therapy bags, has led to injury or death in patients. This system can significantly reduce even the possibility of such problems. In addition to carefully identifying the materials, sources, patients, dosage, and rates for use of the prescription, that information can be used upon reading of the information on the chip to assure that the particular delivery device (which may also include patient identification information and the like) is the proper device through which the prescription is to be delivered. For example, the chip in the FCM may identify the specific administration device (by unit number, model number, location, patient identifier and the like), and that information is compared on site with the information provided by the delivery device. If there is no match between the information, such as where the bag has been misdelivered or the wrong chip inserted, an alarm or other notification to the potential user would indicate an error. The degree of the error would determine whether or not the programmed delivery would occur.

Figure 2:
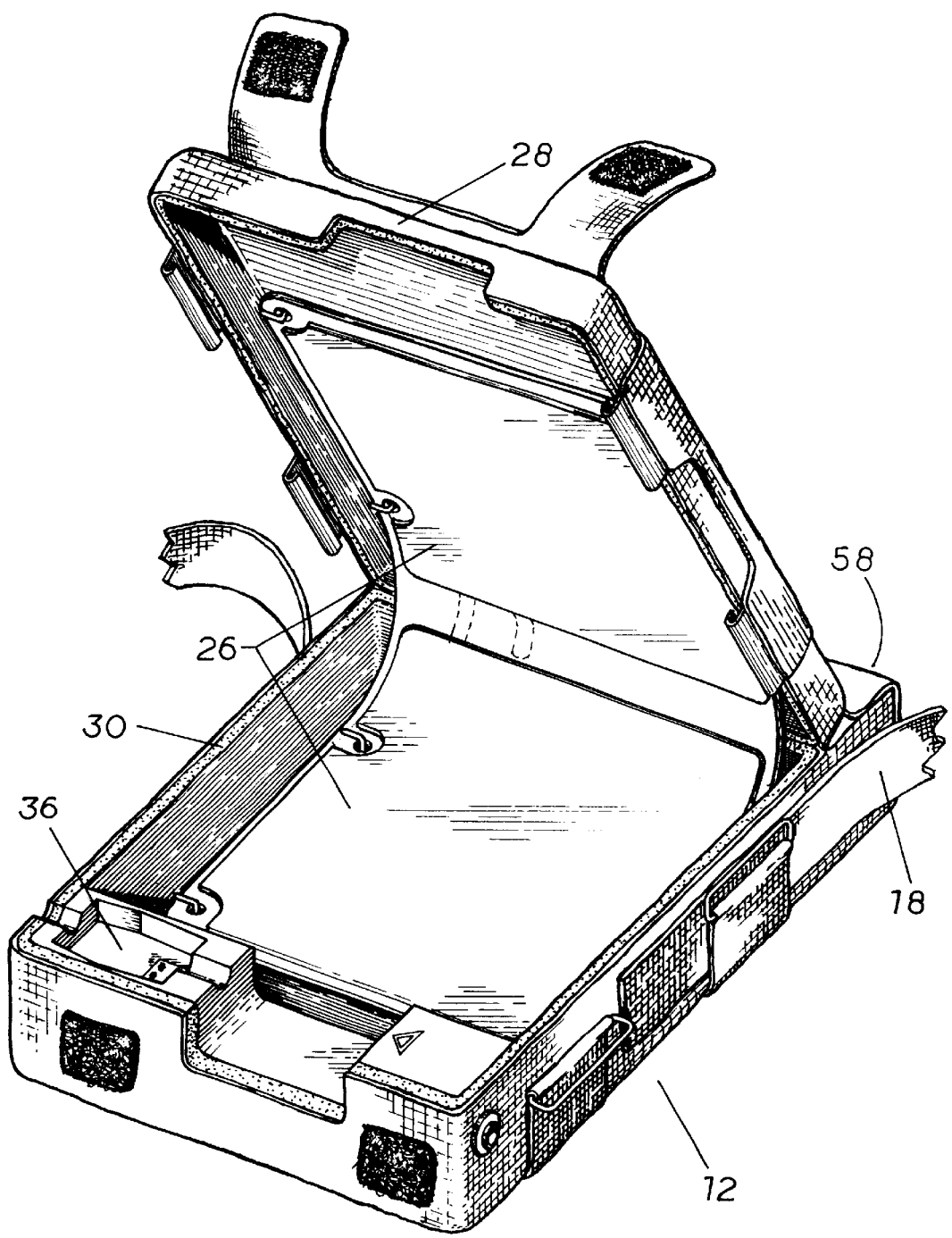
FIG. 2 is a drawing of the infusion system of FIG. 1 in the open position.

Referring to FIG. 1, an assembled infusion system 10 includes a pump unit 12, the fluid control module (FCM) 14 docked in a pocket of the pump 12, a partial view of the set 16, shoulder straps 18 for supporting the pump 12, a display 20 part of an electronic control unit (ECU) 22. FIG. 2 shows the interior of the pump unit 12, and FIGS. 2, 3*a*, 3*b* display the components of the infusion system 10 in greater detail. A therapy bag 24, (FIG. 3*a*) shown prior to being loaded into the pump 12, is configured to fit into the pump 12 in contact with a bladder 26 which is anchored to the flap 28 of the pump 12 as well as to the body 30 of the pump 12. When installed in the pump 12, the therapy bag 24 lays between the folded halves of the bladder 26. The bladder 26 is removable from the pump 12 and may be periodically replaced.

Figure 3C:
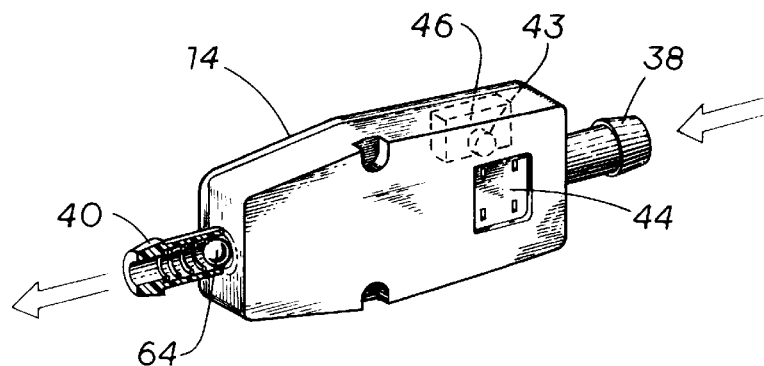
FIG. 3c is a drawing of a first embodiment of a fluid control module of the invention.

The therapy bag 24 is fabricated from a flexible material such as plastic, fabric, or composite materials and contains an input connector 32 used by the pharmacist in filling the bag 24, and an output connector 34 connecting to the set tubing 16. In series with the set tubing 16 is the FCM is 14 inlet port 38 and outlet port 40 connected to a section of set 16 tubing 42 which feeds the medication to the patient. Referring to FIG. 3*c*, the body of the FCM 14 includes a an external electrical connector 44 and an internal socket 43 wired to the connector 44. The plug-in element (here shown in a non-limiting manner to be an EPROM 46) mates with the socket 43. When the pharmacist fills the therapy bag 24 in accordance with the doctor's prescription, he also programs the EPROM 46 by means of his information storage or writing device such as a computer and an associated EPROM writer to contain the essential information related to the prescription. This may include the patient's name, the doctor's name, the name and supplier of the medication, rate of flow and the flow profile as a function of time for dispensing the medication, checking the medication viscosity, and a telephone dial-up program to obtain help if the infusion system 10 malfunctions. In the assembled infusion system 10, the FCM 14 docks into the recess 36 located in the body 30 of pump 12 (FIG. 2). The recess 36 contains a connector which mates with the FCM connector 44, and which feeds a flex printed circuit cable 56 running up to an electronic module 48. The electronic a module 48 contains the ECU 22, an LCD display 20, a miniature air compressor 50, a "start" button 52 and a "stop" button 54. The electronic control module 48 is enclosed in the top area 58 of the pump 12 as shown in FIGS. 1, 2 and 3*b*.

Figure 4A:
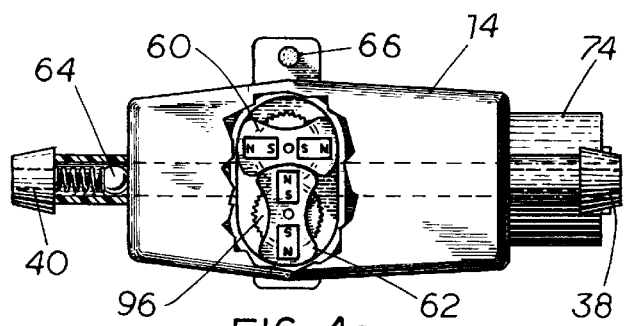
FIGS. 4a, 4b and 4c are drawings of additional views of the fluid control module of FIG. 3c, FIGS. 5a–5b are drawings showing the internal components of the fluid control module of FIG. 3c, FIGS. 6a–6d are schematic drawings illustrating successive positions of the magnets located within the fluid control module of FIG. 3c.
Figures 4B, 4C:
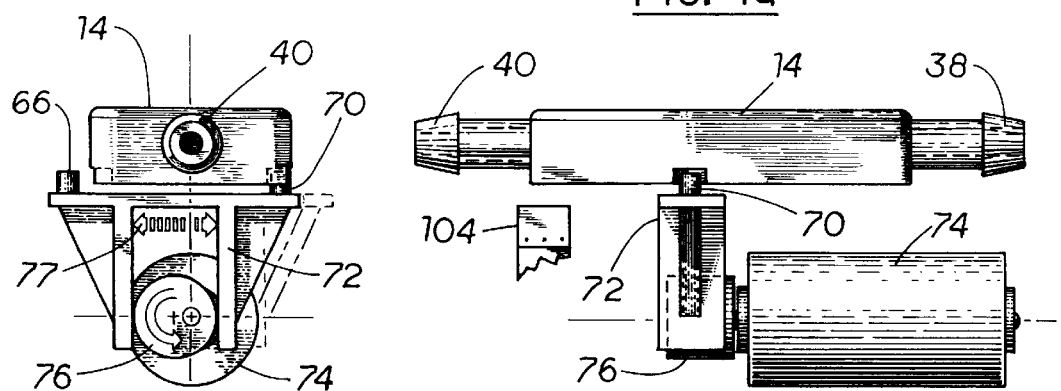

Referring to FIG. 4*a*, the FCM 14, is a preferably nonmagnetic enclosure preferably fabricated from a plastic, composite, or metal in the form of a cavity having top and bottom planar surfaces and shell like side wall. The FCM 14 has an inlet port 38 and outlet port 40, and has two interlocking internal rotors 60, 62 which control the flow of the therapeutic or diet supplemental medicinal fluid. The rotors 60, 62 are identical in shape, having in general hourglass-shaped contours, and their operation and geometrical outlines will be more fully described below. The FCM also has a check valve 64 installed in the outlet port 40. Referring to FIG. 4*b* fixed magnets 66, 70 are mounted on a control linkage 72 positioned below the FCM's 14 body containing the rotors 60, 62. The control linkage 72 is shuttled bi-directionally, as shown by the arrows 77, by the operation of a motor 74 rotating an offset cam 76. The shuttling motion of the control linkage 72 alternately positions one of the magnets 66, 70 adjacent to one of the rotors 60, 62. For each extreme position of the shuttling linkage 72, only one of the magnets 66, 70 is within range to magnetically influence one of the rotors 60, 62.

Figures 5A, 5B:
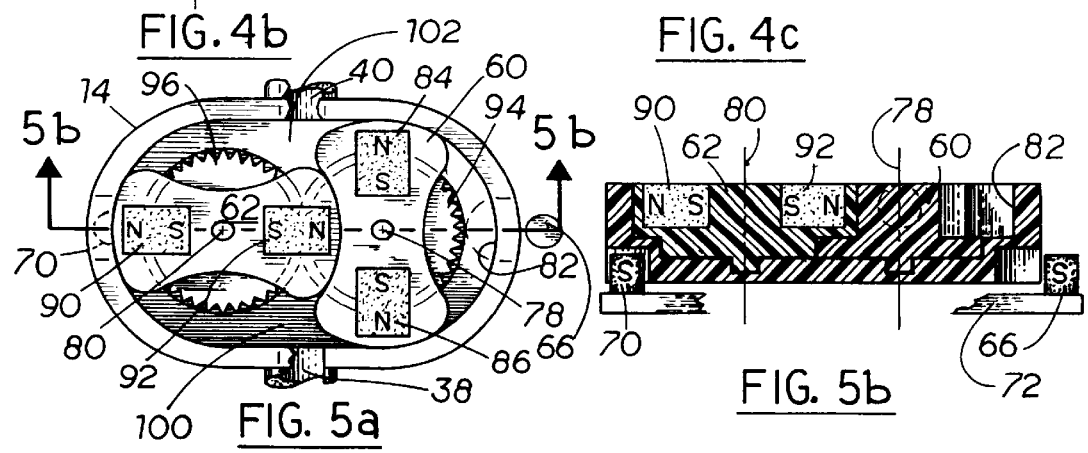

Referring to FIG. 5*a*, the rotors 60, 62 which are molded plastic parts, are shown mounted on rotational axes 78, 80 respectively, positioned within the cavity of the FCM 14. The rotor 60 has magnets 84, 86 and the rotor 62 has magnets 90, 92 longitudinally embedded along the long axes of the rotors 60, 62. The north poles of the magnets 84, 86, 90, 92 are oriented facing the longitudinal ends of the rotors 60, 62. Mounted coaxially about the axes 78, 80 and rigidly connected to the rotors 60, 62 are interlocking spur gears 94, 96, ensuring that both rotors rotate simultaneously, and in counter rotating directions.

In FIG. 5*a*, for the rotor positions depicted, the south pole of the control linkage magnet 70, is oriented so that it is in close proximity to the north pole of the magnet 90 embedded in the rotor 62, while the control linkage magnet 66 is horizontally displaced away from the magnetic structures of the FCM 14. The south pole of magnet 70 is strongly attracted to the north pole of the magnet 90, locking the position of the rotor 62 (and simultaneously locking the rotor 60 due to the intermeshing spur gears 94, 96), keeping both of the rotors 60, 62 immobile. With the inlet port 38 of the FCM 14 connected to a fluid filled therapy bag 24 which is under pressure from the bladder 26, for the locked FCM 14 condition described above no fluid, other than a small controlled "non clotting flow" traversing a small intentional gap 94 between the "in contact" contours of the rotors 60, 62, can flow through the FCM 14.

In open loop operation of the infusion system 10, (FIG. 8), the actual fluid flow to the patient is effected and controlled in the following manner. The electronic control unit 22 executes its internally stored operating system program and the delivery related programmed information stored in the EPROM 46 by the pharmacist, initiating a (for example, time-related parallel) sequence which activates the fluid (e.g., air) compressor (or pump) 50. As the air (fluid) compressor 50 inflates the bladder 26, a pressure transducer 27 internal to the bladder 26 measures the bladder pressure and transmits it to the ECU 22. Stored within the EPROM 46 is the appropriate bladder 26 pressure for dispensing the prescribed medicine from the therapy bag 24 at the correct flow rate, and the cycling rate at which the FCM 14 must operate to effect the proper flow. This portion of the ECU 22 program sends "turn on" pulses to the motor 74 Each pulsation of the motor 74 shuttles the linkage 72 back or forth (77) oscillating the positions of the magnets 66, 70 ( FIGS. 5*a* and 5*b*) relative to the body of the FCM 14 so that either rotor magnet 84 or rotor magnet 86 is attracted to magnet 66 or magnet 70.

Figure 6A:
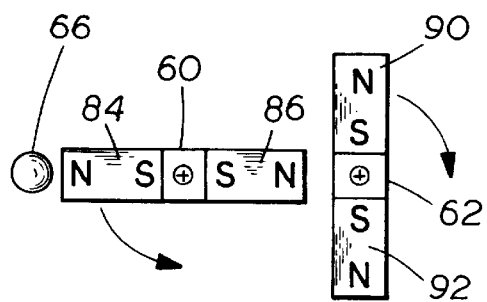
Figure 6B:
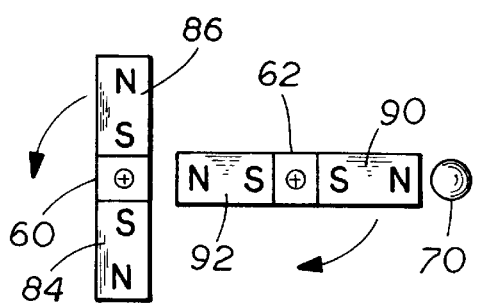
Figure 6C:
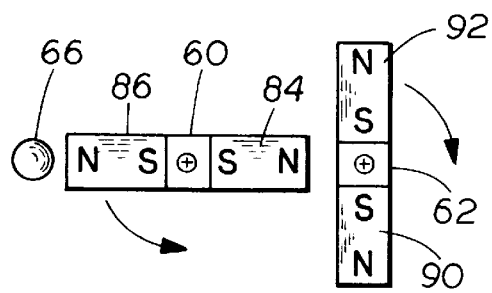
Figure 6D:
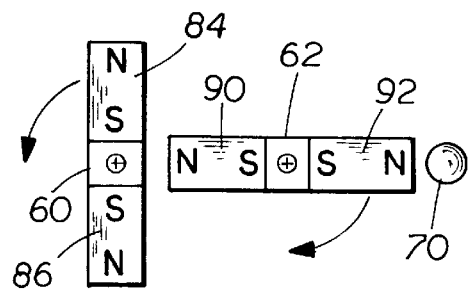

Referring now to FIG. 6*a*–6*d*, the position of the rotors 60, 62 their associated magnets 84, 86, 90, 92, and the control linkage magnets 66, 70 are schematically represented for controlling flow through the FCM 14. FIG. 6*a* shows the positions of the rotors and magnets corresponding to the rotor configuration of FIG. 5*a*. The magnet 66 strongly attracts and holds the magnet 84 stationary, locking the rotor 60 against rotation, and correspondingly locking the rotor 62 coupled by the spur gears 94, 96 to the rotor 60. It is to be noted that the fluid from the therapy bag 24 under pressure from the bladder 26 has filled the inlet cavity 100 (FIG. 5*a*) of the FCM 14. However, flow of the fluid from the inlet cavity 100 is blocked by the stationary rotors 60, 62. Hence, there is no flow of fluid that is contained within the outlet cavity 102 (FIG. 5*a*) of the FCM 14 to the patient through the outlet port 40. For a bolus of medication to flow from the FCM 14, the program of the ECU 22 transmits a "rotate command" to the motor 74 (FIGS. 4*b* and 4*c*) and the motor 74 rotation shuttles the command linkage 72 to shift the magnet 66 from its position proximate the rotor magnet 84. This frees the rotor 60 from the magnetic force of the magnet 66 and allows it to rotate a quarter turn, while the rotor 62 rotates in the opposite direction. Because of the geometrical configuration of the contours of the rotors 60, 62, the fluid pressure within the inlet cavity 102 applies a greater force perpendicular to the moment arm of the rotor which is in contact with the waist of the other rotor, than the fluid pressure applies to the moment arm of the rotor in contact with the shell 82 of the FCM 14. (The moment arm of rotor 60 in contact with the waist of rotor 62, compared to the moment arm of the rotor 60 in contact with the cavity shell 82, in this example). This difference in force causes the "just released" rotor (rotor 60 in this example), to rotate in a counterclockwise direction, while the rotor 62 rotates in a clockwise direction. In the meantime, the magnet 70 has been positioned by the linkage 72 into the position shown schematically in FIG. 6*b*, and after a quarter rotation the magnets 84, 86 of rotor 60 and the magnets 92, 90 are positioned as shown, with the magnet 70 attracting and holding the magnet 90. This quarter rotation has forced a bolus of medication previously in the cavity 102 through the outlet port 40 out into the set connected to the patient. FIGS. 6*c*, 6*d* illustrate sequences of further quarter turns of the rotors 60, 62 each of which provides one bolus of medication to the patient.

Figure 7:
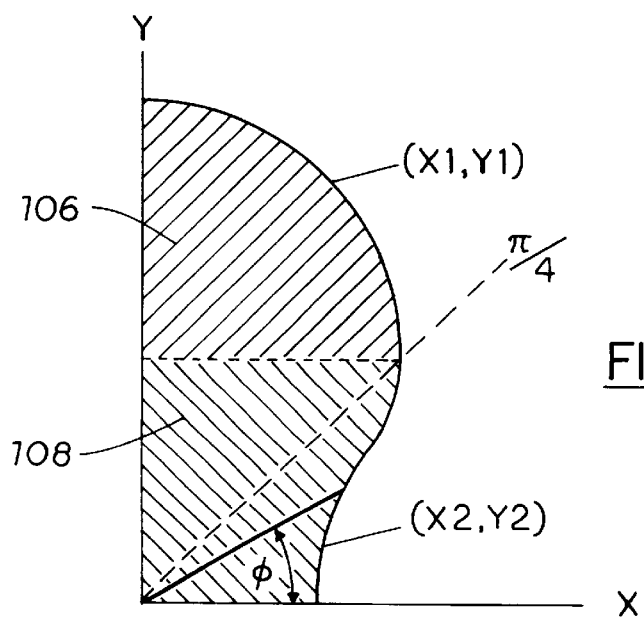
FIG. 7 is a graph of the partial contours of the rotors within the fluid control module of FIG. 3c.

The inner contour of the shell 82 (FIG. 5*a*) consists of two semi-circular end surfaces connected by straight planar segments, and the end faces of the rotors 60, 62 are in intimate contact with the shell contour (82) blocking the passage of fluid at these contact points. The shapes of the rotors 60, 62 are symmetrically cycloidal, and their contours are partial epicycloidal and hypocycloidal curves. Referring to FIG. 7, the contour of the first quadrant of the rotors 60, 62 is shown divided into 2 zones, 106, 108. The angle φ is the angle between the X axis and the curve defining the first quadrant of the rotor 60, 62. In the zone 106 where φ=, π/4 to π/2, and defining the rolling radius that generates the epicycloidal contour as A, the coordinates of the contour XI, Y1 are generated by the equations:

$$X1=5A[\cos \phi]+A[\cos 5\phi] \quad Y1=5A[\sin \phi]+A[\sin 5\phi] \text{ In zone } 108$$
$$\text{where } \phi=\pi/4 \text{ to } 0,$$

with the same rolling radius A, the coordinates X2, Y2 are given by the equations:

$$X2=3A[\cos \phi]-A[\cos 3\phi] \quad Y2=3A[\sin \phi]+A[\sin 3\phi]$$

These equations, when solved for various values of A, yield the first quadrant boundary coordinates as a function φ. From this, one can derive the symmetric complements of the first quadrant to develop the total outside contour of the rotors 60, 62. The above equations are provided as an example of generating the rotor contour; other cycloidal expressions may yield equally valid contours. With the contours determined, the volume of an outlet cavity, i.e. 102, may be determined, and by way of example, in a FCM having rotors 60, 62, ⅛ inch in height, and for a rolling radius A=0.030 inch, the FCM will deliver 0.1851 ml/rev. This provides the flow control constant to the ECU 22 memory allowing the software to establish the volumetric flow per quarter revolution.

The rate of flow of medication is thereby determined by the program of the ECU 22 which controls the command rate to the motor 74. Referring again to FIGS. 4*c* and 8, a Hall effect sensor 104 is positioned in the pump 12 adjacent to the recess 36 in which the FCM 14 is docked. A pulsed electrical output of the Hall effect sensor 104 occurs for each quarter rotation of the FCM rotors 60, 62 due to the changing magnetic fields at the sensor 104. This electrical pulse is monitored by the ECU 22 to confirm that the rotors 60, 62 are actually rotating at the rate set by the ECU 22. It will be noted that if the FCM 14 rotors fail to rotate due to a blockage or due to a failure of the bladder 26 or therapy bag 24 to provide fluid at the pressure necessary to generate the torque required to rotate the rotors 60, 62, no output from the Hall sensor 104 is detected and the ECU 22 activates an alarm. This alarm generates a flashing message on the display 20, as well as an audible alarm from a small speaker mounted in the pump 12. It also deflates the bladder 26 and immobilizes the air compressor 50. Also, if the patient 11 attempts to remove the therapy bag 24 in an unauthorized manner, the ECU 22 activates a relief valve 116 which deflates the bladder 26 and the ECU 22 initiates an alarm subprogram. A further feature of the alarm system which comes into play when the patient 11 is in bed utilizes a modem included in the ECU 22 which is connected to a wall mounted plug-in telephone line. The activation of the alarm causes the ECU 22 to dial up a stored fax or telephone number and to transmit information via the modem from the ECU 22 storage describing the status of the infusion system 10, and summoning help if required.

Figure 8:
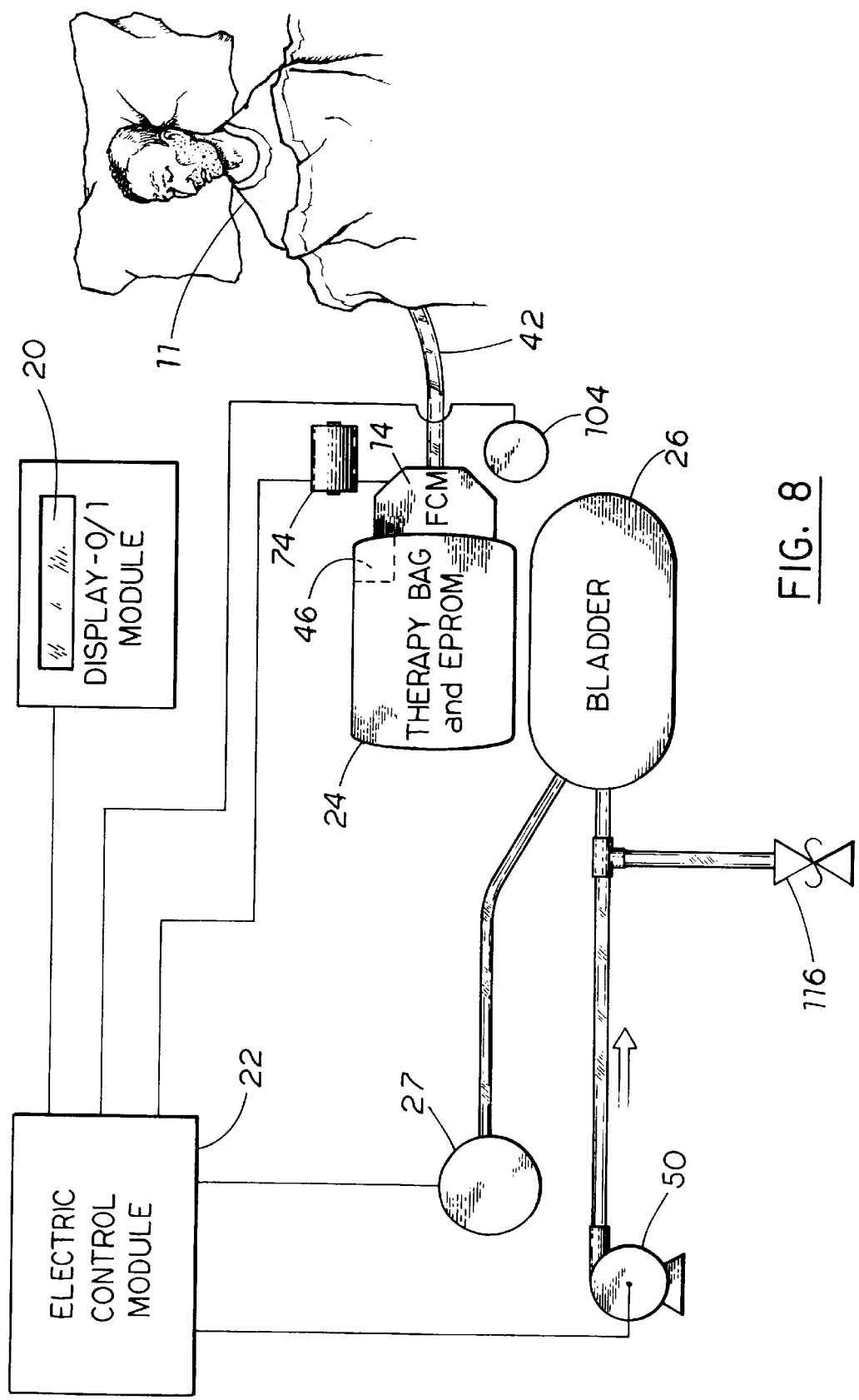
FIG. 8 is a block diagram of the infusion system of the invention.

In a second embodiment, the infusion system of the invention operates closed loop. In this configuration the interconnection between the system elements are substantially the same as shown in FIG. 8, except that the output of the Hall sensor 104 fed back to the ECU 22 is not used simply as a detector of the rotation of the rotors 60,62, but the rotation rate is compared to stored flow rate values in the ECU 22 memory to develop an error signal proportional to the deviation of the flow from the required flow rate. Depending upon the magnitude and sign of this error, the ECU either increases the pressure in the bladder 26, or decreases it by controlling the speed of the air compressor 50, thereby servoing the flow rate to the desired value.

A third embodiment, illustrated in FIGS. 9–13, discloses the FCM 14' as an integral part of the therapy bag 24'. In the drawings, different but related elements are identified by the same reference character, albeit that the different elements are distinguished by primes. In the earlier embodiment of FIG. 3c, the FCM 14 is not integral with the therapy bag 24, but is a separate unit connected to the therapy bag 24 by the set tubing 16. In the third embodiment, the FCM 14' is included in the output connector 34' of the therapy bag 24' (FIGS. 9, 10) and the tubing 42' to the patient connects to the output connector 34' containing the FCM 14'. The therapy bag 24' is filled by means of the input connector 32' and contains an electrical connector 44' connecting with an EPROM (not shown) internal to the therapy bag 24' which performs the same function as the EPROM 46 as previously described above. Associated with the input connector 32' and output connector 34' is a docking element 35 which fits into a mating recess 37' (along with the input and output connectors 32', 34'), in the pump 12' when the therapy bag 24' is assembled with the pump 12'.

Figure 11:
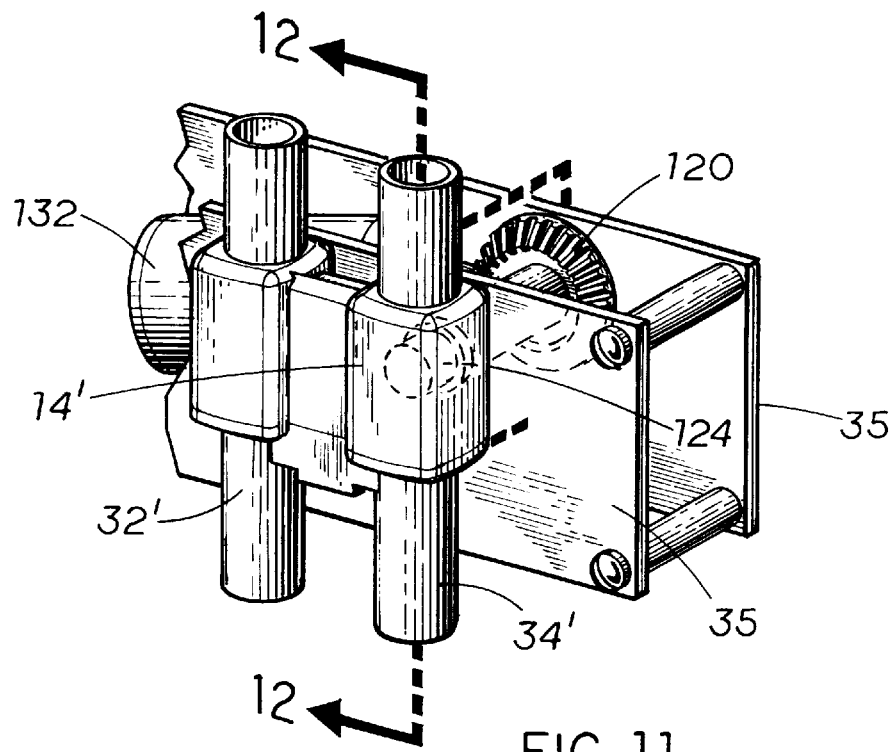
Figure 12:
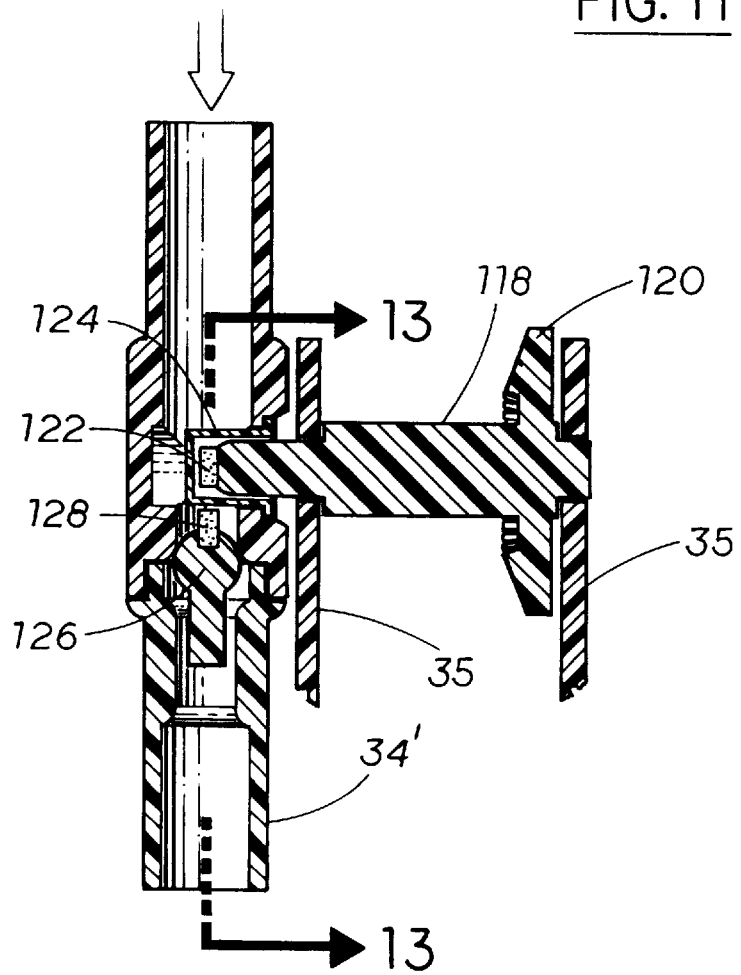
Figure 13:
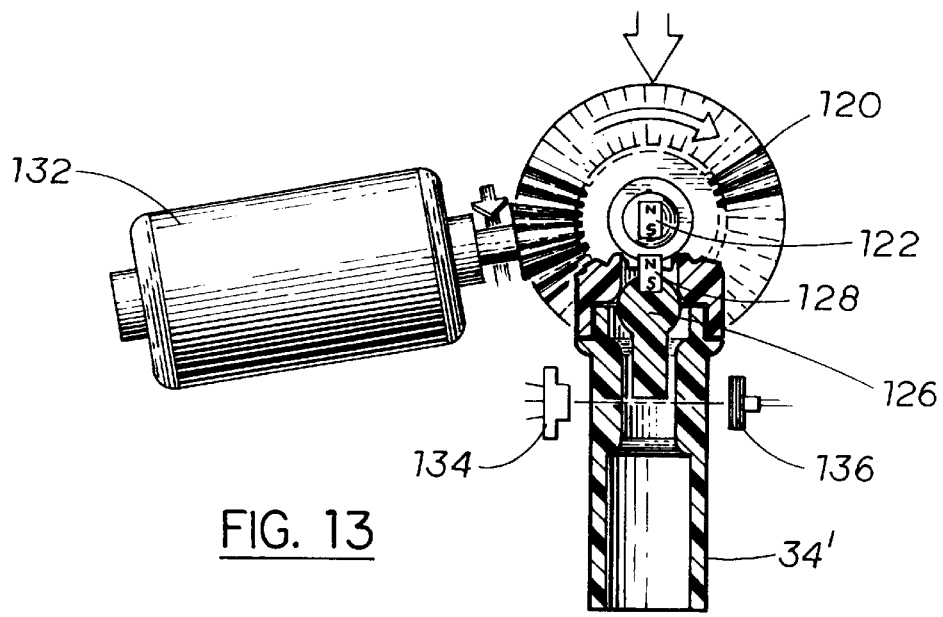

The FCM 141 may be seen by referring to FIGS. 11, 12, 13. Part of the FCM 14' is the docking element 35, which is a fiberglass boxlike structure supporting a shaft 118 having bevel gear 120 mounted on one end of the shaft 118, and a magnet 122 mounted on the other end of the shaft 118. The end of the shaft 118 on which the magnet 122 is mounted, fits into a cylindrical cavity 124 in the side of the output connector 34', however fluid from the therapy bag 24' will flow around the outer walls of the cavity 124. Mounted proximate the cavity 124 in the output connector 34' are the other elements of the FCM 14', i.e., a "cork" 126 having one end bulbous shaped and the other end in the shape of a cylindrical rod, and an associated magnet 128 fitted into the bulbous end of the cork 126. Referring to FIG. 10, the docking element 35, when docked to the mating recess 37, causes the bevel gear 120 to engage a spur gear 130 (FIG. 13) attached to shaft of a drive motor 132. In FIG. 13 the small bar magnet 122 is seen mounted on the opposite end the shaft 118 from bevel gear 120, and when the docking element 35 is engaged in the recess 37, the bar magnet 122 is facially juxtaposed opposite the magnet 128 attached to the cork 126. For the rotation position of the bevel gear 120 shown in FIG. 13, the magnets 122, 128 are seen in attractive positions of N versus S respectively, drawing the cork 126 to block the upper portion of the channel of the output connector 34' (FIG. 14a), thereby operating as check valve denying back flow from the set to the therapy bag 24. The motor 132 operates under control of the ECU 22, which controls flow of the fluid by sending a rotate signal to the motor 132. Upon receipt of a rotate signal, the shaft of the motor 132 rotates 180 degrees, and the spur gear 130 drives the bevel gear 120 through 180 degrees, reversing the orientation of the magnet 122. This cause the magnet 122 to repel the magnet 128 of the cork 126, moving the cork 126 downward (as seen in FIG. 14a) from the check valve position, and allowing the flow of the fluid from the therapy bag 24' around the cork 126 as shown by the dotted lines of FIG. 14b. Under the pressure of the fluid flow the cork 126 moves down in the channel of the output connector 34' until the bulbous portion of the cork 126 snugly mates with the constriction in the channel of the output connector 34' as shown in FIG. 14c. This shuts off the flow from the pump 12', having allowed one bolus of fluid to flow out to the patient. For the next rotation of the bevel gear 120 under control of the motor 132, the magnets 122,128 again attract each other, returning the cork 126 again into the check valve position of FIG. 14a.

Referring again to FIG. 13, a laser led 134 directs a beam of light through transparent walls of the output connector 34' to a photodiode 136. The excitation for the laser led 134, and the output of the photodiode are connected through the electrical connector 44' to the ECU 22. Each time a bolus of medication is transferred out through the output connector 34', the end off the cork 126 interrupts the laser beam and a signal is transmitted to the ECU 22 from photodiode 136. If the ECU signals for a cycle of bolus, and there is no corresponding interrupted light output sensed by photodiode 136 the alarm mode is activated by the ECU 22.

Figure 15:
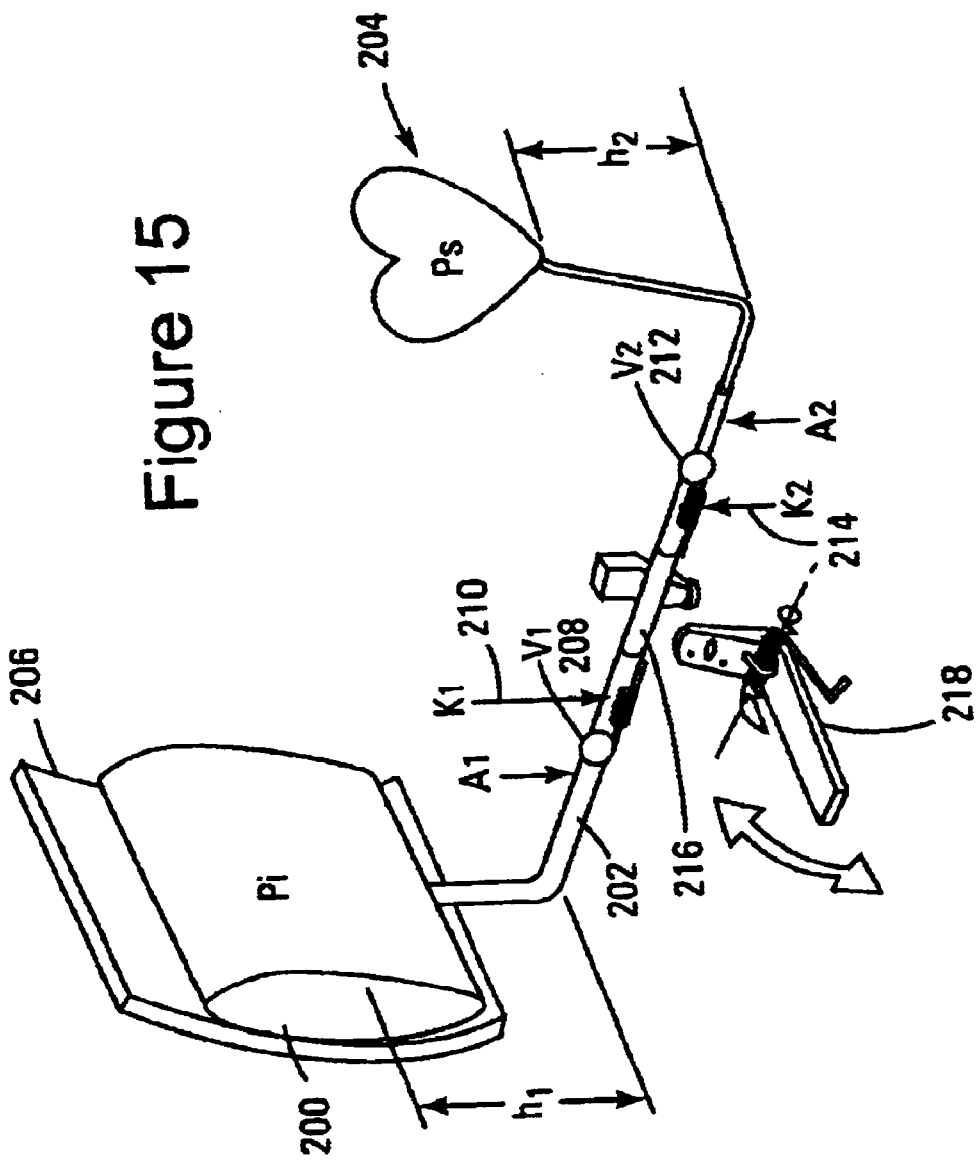
FIG. 15 shows a schematic rendition of an idealized association of a therapy bag and tubing with respect to the heart of a patient (not shown).

FIG. 15 shows a schematic rendition of an idealized association of a therapy bag 200 and tubing 202 with respect to the heart 204 of a patient (not shown). The FIG. 15 may be explained in principle according to the following information.

1. A bladder 206 exerts a measured pressure (Pi) on a therapy bag 200.
2. A pressure head $h_1$ results which is proportional to $h_1-h_2$ (the differential between the upstream pressure in the therapy bag 200 and the downstream head plus heart 204 created fluid pressure ($P_j$).
3. Pi is the fluid pressure within the bag and ($h_1-h_2$) is the operating pressure head. It is this differential in pressures ($P_i-P_j$) which causes the fluid in the bag to flow into or through the infusion system.
4. A check-valve 208 ($V_1$) with an effective area $A_1$ and a return spring 210 (with a flow resisting tension of $K_1$) impedes flow in conjunction with a check-valve 212 ($V_2$) in the effective area $A_2$ along with a return spring 214 (with a flow resisting tension of $K_2$). Customarily, but not absolutely, $A_1 > A_2$ and $K_1 < K_2$. This relationship is important in sizing these components to prevent unwanted flow such as might occur if one were to over pressure Pi by squeezing, or sitting on the bladder.

5. In the operating sequence $V_1$ will permit the flow to commence when the bladder 206 reaches the proper pressure (for the given therapy program and viscosity $\mu$). Fluid will pass thru $V_1$ but $V_2$ will not permit flow since the opening (cracking) force is designed not to permit flow at this instance. An elastic or elastomeric (e.g., latex, rubber or silicone) tube section 216 is designed to expand (e.g., up to a restraining elements, such as a restraining chamber wall or partition element) as a result of the higher upstream pressure Pi. When the tube section 216 is in equilibrium with the upstream head. Still no flow can occur thru $V_2$. At this point, depending on the programmed delivery rate, a slight pause in flow may occur.

6. Since the flow source is stopped for an exact time to control the rate of flow, all systems are idle. This may be for only a part of a second up to several minutes or whatever is the format and detail of a prescription requirement.

7. When flow is again required, a "mouse trap" mechanism 218 will squeeze the tube 216 in an exactly desired angle of deflection. This applied angle and the resulting reduction in tube 216 diameter reduces the tube's 216 volumetric capacity and the fluid will attempt to flow in both directions. The upstream check valve 208 prevents back flow; while the downstream valve 220 under the momentary or transient force of the "mouse trap" opens the downstream valve 220 and permits a given bolus of therapy to flow until down stream equilibrium is attained, at which time, it will also close, preventing back flow of the liquid. The mousetrap mechanism 218 returns to the "set" or open position and the elasticity of the tube and the upstream pressure fills the tube where no reduction in tube 216 diameter is effected, again completing the cycle.

8. Since the bladder pressure is created by pumping a relatively large volumetric area (of fluid, e.g., air or liquid), compared to the bolus volume per cycle, the pressure can remain almost constant for many boli of therapy pumped. The hysteresis loop for pressure level control can be extremely small (for example, from 0.5% or 1% to over to 1% or to 3% or less under design requirements).

9. The cycle is now completed, and the ECU will, through suitable software and automatic programming, continue the infusion program.

10. The accuracy of flow delivery rate in the pump depends on the control of several variables and dependable components. All such equipment is constrained to these limits. The present invention has designed a system that essentially has been reduced to its simplest form.

11. If a problem does occur, such as a crimp on tube or other condition of occlusion, diagnostic sensors detect the problem and inform the user. For example, if an occlusion occurs, the mouse trap mechanism 218 will not go through its complete travel and the current flow through the DC driver will rise and be easily detected and reported. If the condition occurs on, for example, 5 consecutive cycles, an alert or warning signal is provided by the system. Timers, pressures related sensors and positional detectors each have a part in making sure that the pump of the present invention is doing the best possible job of providing drug therapy of any system in the market place at the lowest cost.

The pressure of the bladder forces therapy out of the set bag, through the fluid control module (FCM) and via tubing into the patient's artery (or other designated target delivery area). The control of the rate of flow to the patient is a function of the bladder pressure, the diameters of the tubes, the therapy viscosity, the system losses (friction) and the control apparatus. The apparatus may operate as described above for mechanics, and as amplified below with respect to personal activity.

A. Therapy flows out of the therapy bag or set bag 200 into the exit port (not shown) of the FCM (not shown in this Figure) and is impeded by the first valve 208, but the pressure in the bladder is high enough to override the cracking force required by the valve 208.

B. A second valve 220 could be opened by the flow, but the forces to open the second valve 220 (resulting from a stronger spring, smaller elastic element, smaller force providing mechanism or a smaller seal diameter or one or more) are much, much greater than the bladder pressure can exert and so the flow is stalled.

C. The upstream pressure is sufficient to enlarge the volume of the tube 216 to a level that is equal to that pressure residing in the bladder 206 and controlled by the ECM (not shown), and the pressure sensor (not shown) in line.

D. When this equilibrium condition is attained the mouse-trap mechanism 218 squeezes the control-tube 216 slightly, the measured volume is controlled by the plastic case (not shown) that forms the outer housing of the FCM (not shown). The squeezing action reduces the volume of the control-tube 216 and the fluid tries to escape the confines of the tube 216 through the two valves 208 220. The fluid cannot go upstream since the valve 208 is a full-check valve in this direction.

E. The second valve 220 must open now since the force of the mousetrap mechanism 218 is sufficient to open the second valve 220.

F. The control-tube 216 now contracts to its normal condition permitting a known bolus of therapy to move down the tube 216 toward the user.

G. The size of the bolus and the rate of the cycle have been computed by the ECU (not shown) in accord with the therapy used and the programmed rate required by the Prescription.

H. The cyclic repetition rate, and the interim pauses, of the above steps determine the average flow rate of the system. The rate is capable of covering large variations of fluid delivery requirements with highly accurate results.

I. The pump program can be altered by the patient, if permitted by the program, so that he/she can enable a larger or smaller flow rate to improve or minimize pain that sometimes might occur, which is typical in a narcotic administration system within modem hospital facilities. This is referred to as Patient Controlled Analgesia, (PCA). In addition, a standard leak is programmed into the delivery because very small bolus is required to be delivered through the tube 216, at well known rates, to prevent clotting at the tube connections.

If any malfunction, such as a kinked tube, e.g., should occur, the expandable chamber (e) will not contract in the expected time and an alarm will sound and a diagnostic displayed. This kind of anomaly data is stored in the pump memory for later automatic down loading. It is suggested that this download be a part of the normal infusion sequence to serve as historical evidence.

The alternate FCM system described above will also pass the basic design criteria demanded by the system design parameters that were delineated at the start of this disclosure. These systems have been modeled and their operation tested.

Figure 16A:
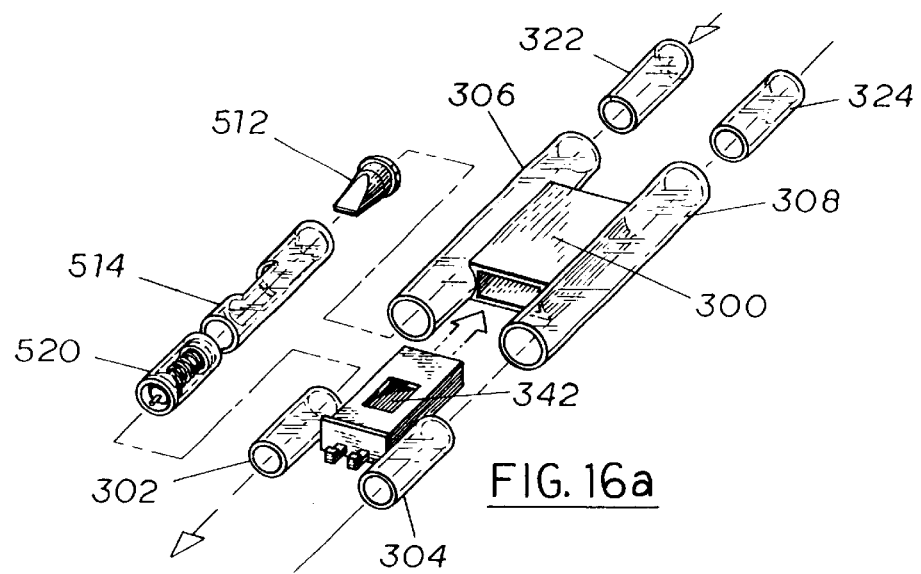
FIGS. 16a, 16b and 16c show a perspective view of elements of the system of the invention as used in a series of steps engaging a fluid control module.
Figure 16B:
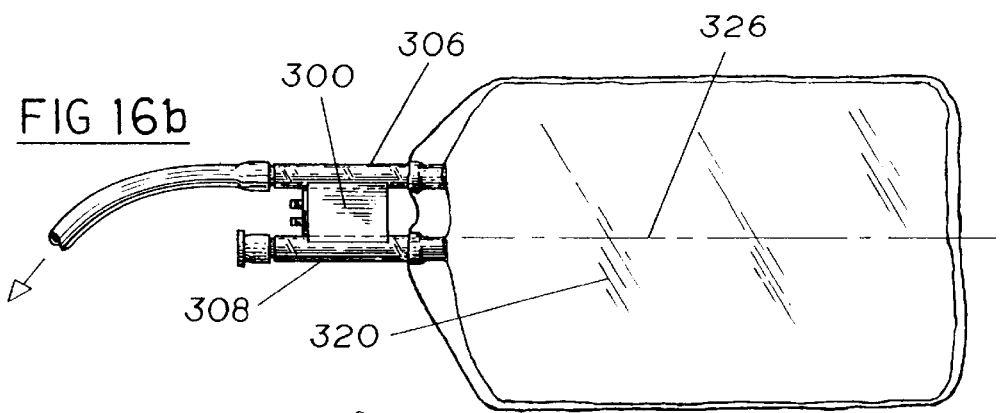
Figure 16C:
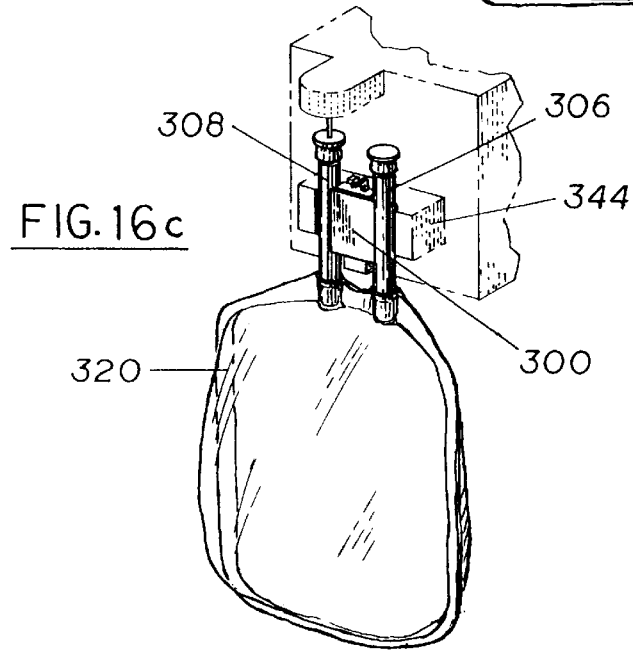

FIGS. 16a, 16b and 16c show assembly mechanisms for various elements of the invention. FIG. 16a shows a fluid control module 300 with stub tubes 302 and 304 positioned for insertion into openings 306 and 308 in the FCM assembly 300. The stub tubes 302 and 304 and 324 and 322 are likewise connected to openings 308 and 306 in some manner of physical connection, as may be, for example only, by snap fit, fusion, or adhesive securement into position, but are preferably adhesively secured, as with a radiation sensitive or thermally sensitive adhesive. In FIG. 16b, a flexible bag 320 is shown radio frequency (R.F.) welded to the two ports 322 and 324 to the fluid control module 300. Note the eccentricity of the two ports 322 and 324 with respect to a symmetry line 326 in the bag 320 to insure that the bag 320 is positioned properly within the pump 364. FIG. 16c shows a flexible bag with attached fluid control module 340 with the chip 342 being accessed by an electronic information reading system 344 accessing the chip 342 through electrical connections or ports (not shown).

Figure 17A:
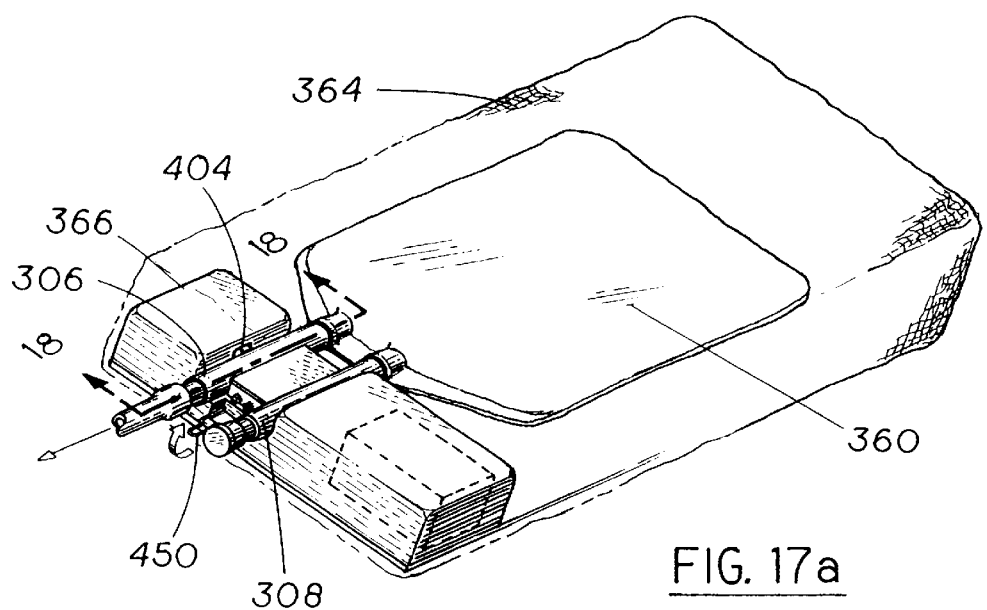
FIGS. 17a)–17c) show a perspective view of separate components which may be used in an example of a fluid control assembly similar to that shown in FIG. 16.
Figure 17B:
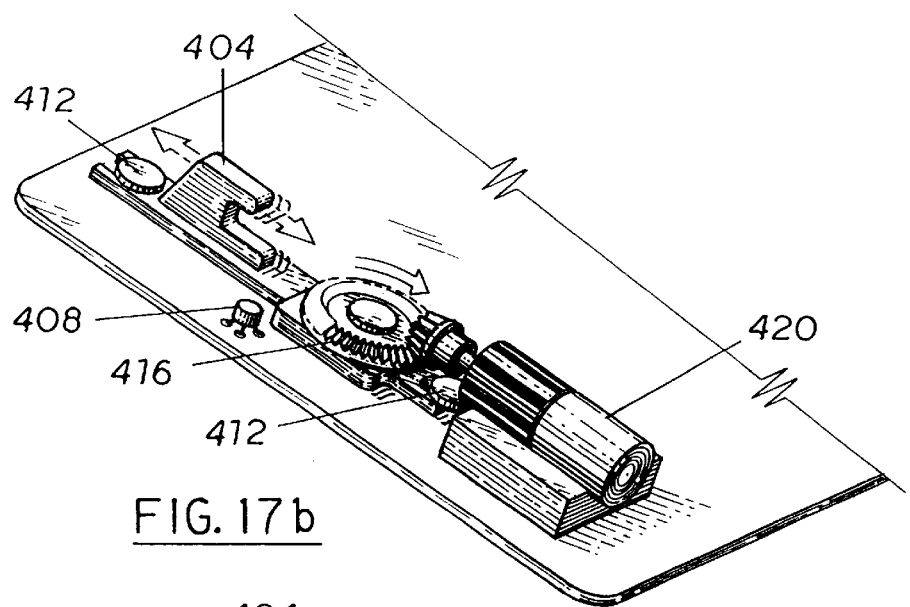
Figure 17C:
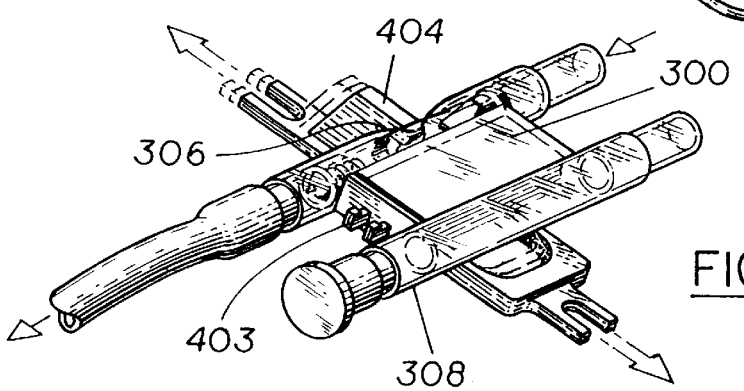

FIGS. 17a, 17b and 17c show a perspective view of the elements of the system of the invention as used in a series of steps engaging a fluid control module 300. A patient drops (inserts) the flexible bag 360 with the fluid control module 300 affixed thereto into the pump 364. The bag 360 and the FCM 300 are locked into the pump 364 so that additional operations may be automatically performed. Information in the chip 342 (in FIG. 16a) is downloaded into the pump 364 which has its own memory/read system 366. FIG. 17c shows two hook elements 403 that cooperate with a bale 450 to latch the fluid control module to the dock 366. The act of latching may accomplish at least two objectives: 1) The latching may complete or activate a connection to turn on a visual signal (such as an LED, e.g., a green LED) to indicate that the fluid control module in the correct position and the unit is actively "on" for dispensing the treatment. 2) The latching may also operate to permit the bladder to hold air an still operate. When the bale 450 is removed, it opens the valve, letting the bladder release any entrapped air so that the bag can be withdrawn. FIG. 17c shows a locking mechanism for the engagement of a tube (not shown in this Figure) with the receptor system 400 of the pump (not shown in this Figure). One method of operation for this aspect of the system would be the use of a precision cam that rotates one turn per stroke. This would act like a modified "Scotch" yoke. Each stroke would depress the volume of the exit tube. When the slider retreats from the tube, the bladder would force the fluid to fill the vacant volume. This is a very accurate procedure. A slide 404 engages a guide pin 412 to control its displacement path. The slide 404, upon reaching the end of its travel, actuates a sensor that logically informs the controller of its position. That position is then compared against a clock to manage the fluid flow rate. If the rate varies from a normal flow rate or a programmed comparison rate or programmed directed flow rate, as would be the case where a tube was kinked, the slide 404 would be arrested for security reasons. The slide is shown in this example to be driven by bevel gear set 416, and powered by a miniature DC motor with a gear train 420. FIG. 17c shows a tube 306 squeezed by the slide 404. The slide 404 engages the tube 306, squeezing the tube 306 at a precise pressure and at a precise rate and displacement.

Figure 18:
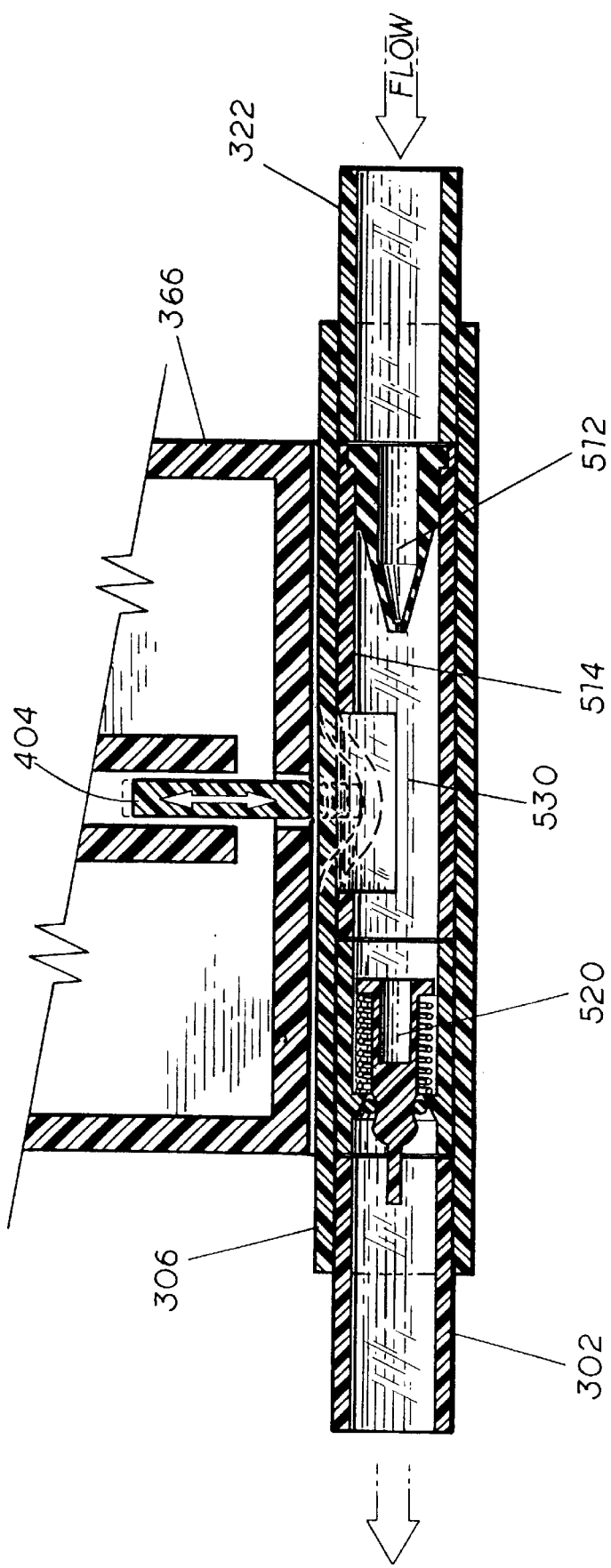
FIG. 18 shows a cut-away, side view of one of a number fluid control valve assemblies useful in the practice of the present invention.

FIG. 18 shows a cut-away view of separate components which may be used in an example of a fluid control valve assembly similar to that shown in FIG. 17. The connecting system 500 between a tube 322 from the therapy bag (not shown) to the tube 306 in the fluid control module 300 and the tube 302 for (for example) intravenous delivery of therapeutic liquid (not shown) to a patient (not shown) is secured in a docking support 366 having other desirable components therein. A check valve 512 is shown nesting against and sealing with an abutting lip of the valve spacer 514 on the interior of the docking support 366 towards the proximal end 516 of the fluid control module 300. Towards the distal end 518 of the fluid control module there is a control valve 520 whose operation is elsewhere more particularly described. The control valve 520 engages an exit tube 302 for delivery of the therapeutic liquid. After and during engagement of the therapy bag with the fluid control module in the pump, data within a memory chip (not shown in this Figure) is engaged and a read. The programmed data insures the safety of the patient with respect to operation and delivery of the therapy in the bag. If the wrong bag or wrong prescription is put in the pump, the pump shuts down at least delivery functions. The data read from the chip sets up delivery and pumping parameters, and may even direct changes to be performed in the sequence of time or events in the delivery process (e.g., changing flow rates after an initial rate of delivery, changing delivery rates over the course of time of the day, etc.).

An upstream pressure (e.g., from the pump) drives the therapeutic fluid through the check valve 512 and into the chamber 530 connecting the control valve 520 and the exit tube 302. The chamber 530 is preferably a known, fixed volumetric quantity. The FCM tube, preferably being an elastomeric material, will expand to fill the chamber because of the memory (elastic memory) of the tube and fluidic pressure. An actuator 404 will squeeze the tube 306 while the check valve 512 prevents fluid flow toward the bag (not shown). A control valve 520 (in any type of known construction) operates to prevent flow to the user unless there is pressure in the chamber sufficient to activate or overcome the control valve 520. The pressure must reach a predetermined level, much greater than that provided by the bladder in the pump. The actuator accomplishes that increase in pressure on the fluid within the chamber 530. Even simple constructions of control valves have proven to be very accurate, even with relatively low flow rates.

The pump is quiet, operates (for example only) on 4.7 volt DC current (low voltage is below 10 volts). The pump should be able to operate without bladder pressure as long as the fluid flow into the chamber is not interrupted (e.g., the priming amount of fluid is not achieved or is lost). The use of the actuator will also facilitate the use of patient controls on the flow of therapeutic (including pain control or analgesic materials) materials to the patient. The data can therefore control a standard flow amount of fluid to the patient, but the patient can modify the rate of delivery up to a maximum level, controlled by the Rx data.

What is claimed is:
1. A therapy infusion apparatus for delivery of a therapeutic fluid to a patient, the apparatus comprising:
   a) a flexible therapy bag,
   b) a moveable surface comprising an inflatable bladder which can apply force to an outside surface of the therapy bag, wherein the inflatable bladder is inflatable by a fluid, c) an exit port in said therapy bag comprising a memory unit storing information relating to at least one of identification of a patient and name of medication which therapy bag will allow fluid to exit in a delivery direction from said flexible therapy bag under pressure, and d) an adjustable, fluid control element located along said delivery direction, after said exit port.

2. The therapy infusion apparatus of claim 1 wherein said therapy bag has at least one major face which comprises at least 25% of the total surface area of said therapy bag, and said movable surface can be moved into contact with said at least one major surface so that contact between said at least one major surface and said movable surface covers at least 50% of the surface area of said at least one major surface by the time that said movable surface is fully extended.

3. The therapy infusion apparatus of claim 1 wherein said therapy bag comprises at least two flow ports within a fluid control element, one of said ports comprising said exit port, and adjacent to at least one of said ports is a storage area for a memory unit and access ports for accessing information from said memory unit.

4. The therapy infusion apparatus of claim 3 wherein said memory unit comprises a chip, and the access ports enable electronic connection from an outside memory reading or memory writing apparatus to said chip.

5. The therapy infusion apparatus of claim 4 wherein the chip is present within said storage area, and said chip contains readable information relating to at least two different topics of information selected from the group consisting of a prescription for a therapeutic material; the name of an active ingredient in the prescription; the chemical name of a prescription carrier; additives in the prescription; volume of the prescription; expiration date; name of a prescribing doctor; name of a local supplier or manufacturer of ingredients in the prescription; source of at least some materials in the prescription; a name of a therapy bag manufacturer; a name of a pharmacist; a patient name; patient information relating to at least one of age, allergies, address, frequency of prescription refill, weight, and chemical intolerances; instructions for a flow control module with respect to desired flow rates; intervals for delivery; rate and volume of delivery; and drip rate.

6. The infusion apparatus of claim 1 wherein said fluid is a liquid, which moves said moveable surface of the bladder against a surface of the therapy bag.

7. The therapy infusion apparatus of claim 1 further comprising a microcomputer for controlling at least one operating function of said infusion apparatus.

8. The therapy infusion apparatus of claim 1 wherein said memory chip in said infusion therapy apparatus is programmable by an auxiliary computer external to said infusion apparatus, whereby information may be entered for storage in said memory chip relating to said therapeutic fluid.

* * * * *